United States Patent
Rubenstein

(10) Patent No.: US 10,295,548 B2
(45) Date of Patent: May 21, 2019

(54) ULTRASENSITIVE ASSAY FOR TAU AND METHODS OF USE THEREOF FOR ASSESSING TRAUMATIC BRAIN INJURY IN TISSUES AND BIOFLUIDS

(71) Applicant: The Research Foundation for State University of New York, Albany, NY (US)

(72) Inventor: Richard Rubenstein, Staten Island, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 772 days.

(21) Appl. No.: 14/871,232

(22) Filed: Sep. 30, 2015

(65) Prior Publication Data

US 2016/0091503 A1    Mar. 31, 2016

Related U.S. Application Data

(60) Provisional application No. 62/057,750, filed on Sep. 30, 2014.

(51) Int. Cl.
| | | |
|---|---|---|
| *C12Q 1/6804* | (2018.01) | |
| *G01N 33/58* | (2006.01) | |
| *G01N 33/68* | (2006.01) | |

(52) U.S. Cl.
CPC ....... *G01N 33/6896* (2013.01); *C12Q 1/6804* (2013.01); *G01N 33/58* (2013.01); *G01N 2333/47* (2013.01); *G01N 2333/4709* (2013.01); *G01N 2458/10* (2013.01)

(58) Field of Classification Search
None
See application file for complete search history.

(56) References Cited

U.S. PATENT DOCUMENTS

2003/0036182 A1* 2/2003 Shao .................. C07K 14/31
435/188.5

OTHER PUBLICATIONS

Rubenstein et al. Journal of Neurotrauma 2014; DOI:10.1089/neu.2014.3548. (Year: 2014).*
Chang et al. Journal of Virological Methods 2009; 159: 15-22. (Year: 2009).*
Yang et al. Analytical Chemistry 2007; 79: 3320-3329. (Year: 2007).*
Kobori et al. Analytical Sciences 2009; 25: 1381-1383. (Year: 2009).*
Akter et al. Analytical Biochemistry 2011; 416: 174-179. (Year: 2011).*
Lu et al. Biosensors and Bioelectronics 2012; 33: 216-221. (Year: 2012).*
Urya, Kunihiro et al., "Multiple proteins implicated in neurodegenerative diseases accumulate in axons after brain trauma in humans", Experimental Neurology, 208: 185-192 (2007).
Vos, P.E. et al., "Glial and neuronal proteins in serum predict outcome after severe traumatic brain injury", Neurology, 62: 1303-1310 (2004).
Wang, Jian-Zhi et al., "Kinases and phosphatases and tau sites involved in Alzheimer neurofibrillary degeneration", European Journal of Neuroscience, 25: 59-68 (2007).
Woertgen, Chris et al., "Neuron-Specific Enolase Serum Levels After Controlled Cortical Impact Injury in the Rate", Journal of Neurotrauma, 18(5): 569-573 (2001).
Acker, Christopher M. et al., "Sensitive quantitative assays for tau and phospho-tau in transgenic mouse models", Neurology of Aging, 34: 338-350 (2013).
Bulut, M. et al., "Tau Protein as a Serum Marker of Brain Damage in Mild Traumatic Brain Injury: Preliminary Results", Advances in Therapy, 23(1): 12-22 (2006).
Chang, Binggong et al., "Surround optical fiber immunoassay (SOFIA): An ultra-sensitive assay for prion protein detection", Journal of Virological Methods, 159: 15-22 (2009).
Chiu, Wen-Ta et al., "The impact of time, legislation, and geography on the epidemiology of traumatic brain injury", Journal of Clinical Neuroscience, 14: 930-935 (2007).
Czeiter, Endre et al., "Brain Injury Biomarkers May Improve the Predictive Power of the IMPACT Outcome Calculator", Journal of Neurotrauma, 29: 1770-1778 (2012).
Dawson, Hana N. et al., "Inhibition of neuronal maturation in primary hippocampal neurons from tau deficient mice", Journal of Cell Science, 114: 1179-1187 (2001).
Diaz-Arrastia, Ramon et al., "Acute Biomarkers of Traumatic Brain Injury: Relationship between Plasma Levels of Ubiquitin C-Terminal Hydrolase-L1 and Glial Fibrillary Acidic Protein", Journal of Neurotrauma, 31:19-25 (2014).
Franz, G. et al., "Amyloid beta 1-42 and tau in cerebrospinal fluid after severe traumatic brain injury", Neurology, 60: 1457-1461 (2003).
Gabbita, S. Prasad et al., "Cleaved-Tau: A Biomarkers of Neuronal Damage after Traumatic Brain Injury", Journal of Neurotrauma, 22(1): 83-94 (2005).
Hanger, Diane P. et al., "Novel Phosphorylation Sites in Tau from Alzheimer Brain Support a Role for Casein Kinase 1 in Disease Pathogenesis", The Journal of Biological Chemistry, 282(32): 23645-23654 (2007).
Honda, Masahiro et al., "Serum Glial Fibrillary Acidic Protein is a Highly Specific Biomarkers for Traumatic Brain Injury in Humans Compared with S-100 B and Neuron-Specific Enolase", The Journal of Trauma Injury, Infection, and Critical Care, 69(1): 104-109 (2010).
Johnson, Victoria E. et al., "Traumatic brain injury and amyloid-β pathology: a link to Alzheimer's disease", Neuroscience, 11: 361-370 (2010).
Johnson, Victoria E. et al., "Widespread Tau and Amyloid-Beta Pathology Many Years After a Single Traumatic Brain Injury in Humans", Brain Pathol., 22(2): 142-149 (2012).

(Continued)

*Primary Examiner* — Angela M. Bertagna
(74) *Attorney, Agent, or Firm* — Howson & Howson LLP; Kathleen D. Rigaut

(57) ABSTRACT

Compositions and methods for accurate and sensitive quantitation of T-tau and P-tau are disclosed.

12 Claims, 9 Drawing Sheets

Specification includes a Sequence Listing.

(56) References Cited

OTHER PUBLICATIONS

Kavalci, Cemil et al., "The value of serum tau protein for the diagnosis of intracranial injury in minor head trauma", American Journal of Emergency Medicine, 25: 391-395 (2007).
Lee, Virginia M-Y et al., "Neurodegenerative Tauopathies", Annu. Rev. Neurosci., 24: 1121-159 (2001).
Lewis, Jada et al., "Neurofibrillary tangles, amyotrophy and progressive motor disturbance in mice expressing mutant (P301L) tau protein", Nature Genetics, 25: 402-405 (2000).
Li, Lucia M. et al., "Cross-Sectional Analysis of Data from the U.S. Clinical Trials Database Reveals Poor Translational Clinical Trial Effort for Traumatic Brain Injury, Compared with Stroke", PLoS ONE, 9(1): e84336. doi:10.1371/journal.pone.0084336 (2014).
Liliang, Po-Chou et al., "Proteins in Serum Predict Outcome After Severe Traumatic Brain Injury", Journal of Surgical Research, 160: 302-307 (2010).
Liliang, Po-Chou et al., "Relationship between injury severity and serum tau protein levels in traumatic brain injured rats", Resuscitation, 81: 1205-1208 (2010).
Ma, Marek et al., "Serum cleaved tau does not predict postconcussion syndrome afer mild traumatic brain injury", American Journal of Emergency Medicine, 26: 763-768 (2008).
Magnoni, Sandra et al., "New Perspectives on Amyloid-B Dynamics After Acute Brain Injury", Arch. Neurol., 67(9): 1068-1073 (2010).
Mattsson, Niklas et al., "Refeence measurement procedures for Alzheimer's disease cerebrospinal fluid biomarkers: definitions and approaches with focus on amyloid B42", Biomarkers Med., 6(4): 409-417 (2012).
McKee, Ann C. et al., "Chronic Traumatic Encephalopathy in Athletes: Progressive Tauopathy After Repetitive Head Injury", J. Nueropathol. Exp. Neurol., 68(7): 709-735 (2009).
McKee, Ann C. et al., "The spectrum of disease in chronic traumatic encephalopathy", Brain, 136: 43-64 (2013).
Mondello, Stefania et al., "all-Spectrin Breakdown Products (SBDPs): Diagnosis and Outcome in Severe Traumatic Brain Injury Patients", Journal of NeurotrAuma, 27: 1203-1213 (2010).
Mondello, Stefania et al., "Glial Neuronal Ratio: A Novel Index for Differentiating Injury Type in Patients with Severe Traumatic Brain Injury", Journal of Neurotrauma, 29: 1096-1104 (2012).
Morris, Meaghan et al., "The Many Faces of Tau", Neuron, 70: 410-426 (2011).
Nowak, L.A. et al., "Dementia in a retired world boxing champion: case report and literature review", Clinical Neuropathology, 28: 275-280 (2009).
Okonkwo, David O. et al., "GFAP-BDP as an Acute Diagnostic Markers in Traumatic Brain Injury: Results from the Prospective Transforming Research and Clinical Knowledge in Traumatic Brain Injury Study", Journal of Neurotrauma, 30: 1490-1497 (2013).
Omalu, Bennett I. et al., "Chronic traumatic encephalopathy in a professional American wrestler", Journal of Forensic Nursing, 6: 130-136 (2010).
Ost, M. et al., "Initial CSF total tau correlates with 1-year outcome in patients with traumatic brain injury", Neurology, 67: 1600-1604 (2006).
Papa, Linda et al., "Ubiquitin C-terminal hydrolase is a novel biomarker in humans for severe traumatic brain injury", Crit. Care Med., 38(1): 138-144 (2010).
Papa, Linda et al., "Elevated Levels of Serum Glial Fibrillary Acidic Protein Breakdown Products in Mild and Moderate Traumatic Brain Injury Are Associated with Intracranial Lesions and Neurosurgical Intervention",Annals of Emergency Medicine, 59(6): 471-483 (2012).
Papa, Linda et al., "Serum levels of ubiquitin C-terminal hydrolase distinguish mild traumatic brain injury from trauma controls and are elevated in mild and moderate traumatic brain injury patients with intracranial lesions and neurosurgical intervention".
Pelinka, Linda E. et al., "Glial Fibrillary Acidic Protein in Serum After Traumatic Brain Injury and Multiple Trauma", J. Trauma, 57: 1006-1012 (2004).
Rajput, A et al., "Parkinsonism, Lrrk2 G2019S, and tau neuropathology", 67: 1506-1508 (2006).
Rankin, Carolyn A., "Tau phosphorylation by GSK-3B promotes tangle-like filament morphology", Molecular Neurodegeneration, 2: 12 (2007).
Rostami, Elham et al., "A model for mild traumatic brain injury that induces limited transient memory impairment and increased levels of axon related serum biomarkers", Frontiers in Neurology, 3: Article 115 (2012).
Rothermundt, Matthias et al., "S100B in Brain Damage and Neurodegeneration", Microscopy Research and Technique, 60: 614-632 (2003).
Rubenstein, Richard et al., "A novel method for preclinical detection of PrpSc in blood", Journal of General Virology, 91: 1883-1892 (2010).
Rubenstein, Richard et al., "Prion Disease Detection, PMCA Kinetics, and IgG in Urine from Sheep Naturally/Experimentally Infected with Scrapie and Deer with Preclinical/Clinical Chronic Wasting Disease", Journal of Virology, 85(17): 9031-9038 (2011).
Rubenstein, Richard et al., "PrpSc detection and infectivity in semen from scrapie-infected sheep", Journal of General Virology, 93: 1375-1383 (2012).
Rubenstein, Richard et al., "Re-Assessment of PrpSc Distribution in Sporadic and Variant CJD", PLoS ONE, 8(7): e66352 (2013).
Santpere, Gabriel et al., "LRRK2 and neurodegeneration", Acta Neuropathol., 117: 227-246 (2009).
Sato, Shinji et al., "Tau-tubulin kinase 1 (TTBK1), a neuron-specific tau kinase candidate, is involved in tau phosphorylation and aggregation", Journal of Neurochemistry, 98: 1573-1584 (2006).
Schweitzer, Barry et al., "Immunoassays with rolling circle DNA amplification: A versatile platform for ultrasensitive antigen detection", PNAS, 97(18): 10113-10119 (2000).
Shahim, Pashtun et al., "Blood Biomarkers for Brain Injury in Concussed Professional Ice Hockey Players", JAMA Neurology, 71(6): 684-692 (2014).
Sivanandam, Thamil et al., "Traumatic brain injury: A risk factor for Alzheimer's disease", Neuroscience and Biobehavioral Reviews, 36: 1376-1381 (2012).
Smith, Douglas H. et al., "Chronic neuropathologies of single and repetitive TBI: substrates of dementia?", Nat. Rev. Neurol., 9(4): 211-221 (2013).
Smith, C. et al., "Tau immunohistochemistry in acute brain injury", Neuropathology and Applied Neurobiology, 29: 496-502 (2003).

\* cited by examiner

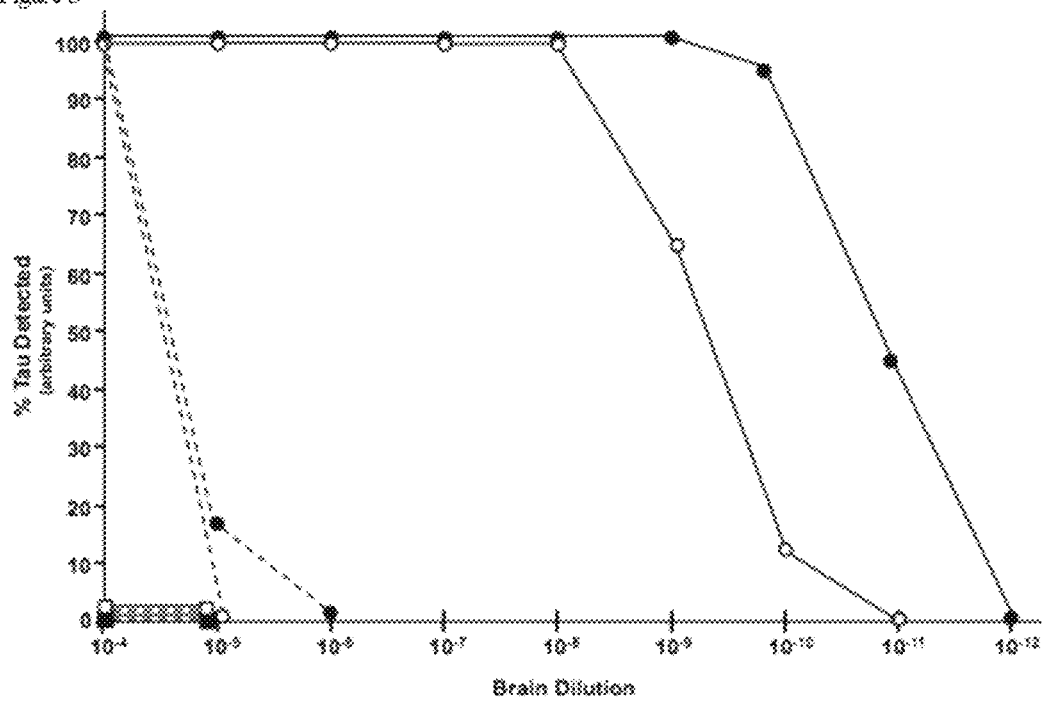

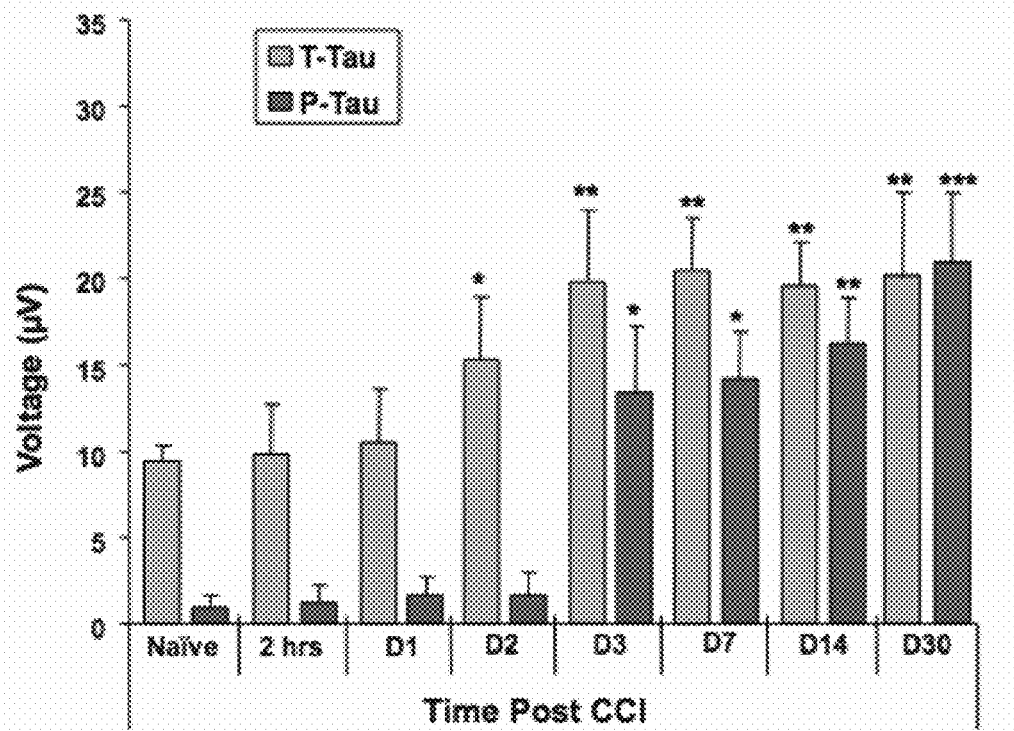

Fig. 6A
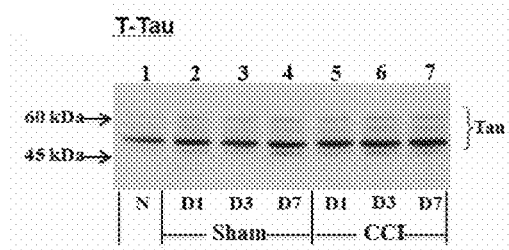
Fig. 6B
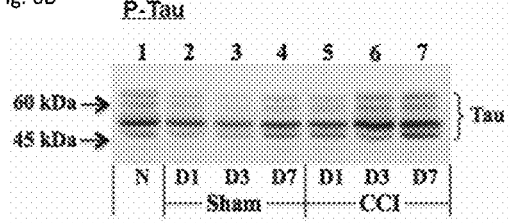
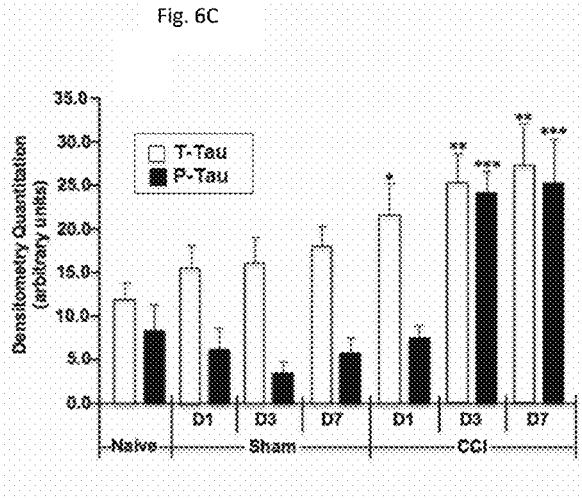

ent protein kinase, glycogen synthase kinase-3β (GSK-3β), cyclic AMP-dependent protein kinase, cyclin-dependent kinase 5 and tau-tubulin kinases (TTBK).[28-32]

SEQUENCE LISTING

<160> NUMBER OF SEQ ID NOS: 1

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
tttttttgtc cgtgctagaa ggaaacagtt ac                                    32

ULTRASENSITIVE ASSAY FOR TAU AND METHODS OF USE THEREOF FOR ASSESSING TRAUMATIC BRAIN INJURY IN TISSUES AND BIOFLUIDS This application claims priority to U.S. Provisional Application No. 62/057,750 filed Sep. 30, 2014, the entire disclosure being incorporated by reference herein as though set forth in full.

FIELD OF THE INVENTION

This invention relates to the fields of neurology and biomarker detection. More specifically, the invention provides a highly sensitive assay for detection and differentiating phosphorylated tau from total tau and correlating levels observed with severity of injury.

BACKGROUND OF THE INVENTION

Several publications and patent documents are referenced in this application in order to more fully describe the state of the art to which this invention pertains. The disclosure of each of these publications and documents is incorporated by reference herein.

Traumatic brain injury (TBI) is one of the leading causes of death and disabilities among all traumas and an increasing body of literature implicates TBI as an independent risk factor for developing Alzheimer's disease (AD).[1-9] The incidence of TBI in the US is comparable to stroke, but affects younger people resulting in a greater health care burden.[10]

TBI covers a wide range of injuries, from mild to moderate and severe. Factors that influence the neuropathology such as the number of repeated impacts, types and extent of injury, and regions of the brain where the trauma occurs have not yet been clearly elucidated. In spite of the fact that most cases of TBI are mild or moderate, most of the TBI animal model systems and studies have focused on severe TBI (sTBI). Even so, reliable predictors of sTBI outcome, particularly during the early stages following neurotrauma, have not been established and are being sought. This emphasizes the need to identify and characterize reliable neurological and biochemical TBI biomarkers for diagnosis and prognosis. Currently, a TBI patient is evaluated only by clinical assessment and neuroimaging, which have their own limitations in predicting the functional impairments associated with the chronic conditions that accompany a significant TBI. Historically, classification of TBI severity has been based on a Glascow Coma Scale (GCS) score, but this widely used clinical neurological score may be influenced by unrelated factors such a patients consumption of drugs or alcohol, prescribed medications and other extracerebral injuries. Therefore, establishing a complementary approach of patient evaluation using neurological assessment in combination with biochemical biomarkers will reliably and objectively determine the severity of a TBI which can then guide treatment regimens.[11-20]

Tau is a microtubule-associated protein localized mainly in neuronal cells and functions as a major structural element in the axonal cytoskeleton. Total tau (T-tau) is abundant in the CNS, and in particular, in unmyelinated axons and cortical interneurons.[21, 22] Under normal circumstances, the phosphorylation of tau (P-tau) is responsible for regulating its biological activity. However, excessive tau phosphorylation (i.e. hyperphosphorylation) is associated with several neurodegenerative diseases and are referred to as tauopathies.[23-25] For example, one of the hallmarks of AD is the presence of neurofibrillary tangles (NFTs) that are composed of P-tau that forms paired helical filaments (PHFs), and also includes increased T-tau and P-tau in the CSF.[22, 26, 27] Pathological phosphorylation of tau has been found at a number of sites including Thr-181, Ser-198, Ser-199, Ser-202, Thr-205, Thr-231, Ser-356, Ser-404 and Ser-422, which are phosphorylated by casein kinases, cyclic AMP-depend The analysis of P-tau is crucial in the diagnosis of AD.[33] However, the significance of P-tau levels following TBI is unclear. Rodent TBI models do not produce NFTs postinjury. However, tau-associated neuropathology, mainly being the presence of NFTs, has been reported in the brains of athletes who have played contact sports (boxers, football and ice hockey players, wrestlers) and who sustained concussions during their career. This pathological condition has been termed Chronic Traumatic Encephalopathy (CTE).[37-42] Common symptoms in CTE include memory loss, Parkinson-like movements, dementia, aggression, confusion and depression.[38, 41, 43-46] Although the majority of CTE cases display widespread NFTs, in contrast to AD, Aβ pathology is less frequent.[42, 47]

Reports on the time course of T-tau and P-tau levels following TBI are limited and include Gabbita et al.[48] and Liliang et al.[49]. We previously described the development of an assay termed SOFIA (Surround Optical Fiber Immunoassay) for the detection of the abnormal prion protein in prion diseased animals and humans.[50-54] As a result of our continued efforts to develop advanced biomarker assay technologies from readily accessible samples, we have changed the term SOFIA to EIMAF (Enhanced Immunoassay using Multi-Arrayed Fiberoptics).

Increased tau levels have been reported in the CSF following TBI and also show promise as a specific serum biomarker in both human patients and experimental models.[13, 15, 16, 34-36] Although there is a rapid rise in tau protein levels in the CSF post-TBI,[13, 34] the peak and temporal progression of serum tau levels have not been adequately evaluated.[15, 16] It is an object of the invention to provide an ultrasensitive assay to facilitate this evaluation.

SUMMARY OF THE INVENTION

In accordance with the present invention, an ultra sensitive assay for quantifying T-tau and P-tau in a biological sample is provided. In a preferred embodiment, the assay is performed for assessing severity of traumatic brain injury (TBI). An exemplary method comprises obtaining a biological sample from a subject and applying EIMAF with antibodies that differentiate P-tau from T-tau coupled with rolling circle amplification, thereby greatly enhancing the sensitivity of the assay, wherein altered levels of P-tau relative to those observed in control subjects are correlated with altered severity of TBI. In certain embodiments, the sample is obtained within one hour of TBI. In other embodiments, the sample is obtained at one hour, one day, one week, two weeks, three weeks, four weeks or six months after injury. In a further aspect, the assay method may further comprise correlating the quantity of P-tau with CT scan normality, or GCS scores.

The assay may also be used to advantage to assess the efficacy of treatments for TBI. In this embodiment, a bio logical sample is obtained before and after treatment with a therapeutic agent and alterations in P-tau levels, if any determined.

BRIEF DESCRIPTION OF THE DRAWINGS

FIG. 3. EIMAF (-) vs. sandwich ELISA (- -) for T-tau (●, ■) and P-Tau (○, □) detection sensitivity. Detection of T-Tau and P-Tau was performed using serial dilutions of JNPL3 (P301L) (●, ○) and TauKO (■, □) mouse brain homogenates. EIMAF has a 5-6 fold more sensitive detection limit than sandwich ELISA.

FIG. 4. Detection of Tau by a-EIMAF in rat serum following sTBI. Adult male Sprague-Dawley rats were subjected to CCI and blood was collected at various time points as indicated. The levels of T-Tau and P-Tau in serum was determined by a-EIMAF. Statistical analysis (t-test) was based on comparison to naïve: * $p<0.001$;  $p<0.0001$; * $p<0.00001$ FIG. 5. Detection of Tau by a-EIMAF in mouse serum following sTBI. CD-1 controls). At days 1 (D1), 3 (D3) and 7 (D7) post CCI or sham treatment, blood was collected and the serum was assayed for T-Tau and P-Tau by a-EIMAF. The levels of T-Tau and P-Tau in the sham-treated mice at D1 (shown), D3 and D7 did not change significantly. Statistical analysis (t-test) was based on comparison to sham-treated: * $p<0.01$;  $p<0.001$; * $p<0.00001$.

FIGS. 6A-6C. Western blotting of mouse brain lysates for Tau. At days 1, 3 and 7 post CCI (or sham treatment), soluble fractions (25 μg) of ipsilateral cortex from CD-1 mouse brain lysates were electrophoresed and western blotted for T-Tau with Mab DA9 (FIG. 6A) and P-Tau with Mab CP13 (FIG. 6B). Western blotting of naive (N) mouse brain lysate was also performed. Shown are representative western blots. Densitometric quantitation (FIG. 6C) of the most intensely immunostained T-Tau (white bars) and P-Tau (black bars) bands was performed using Image J software. Statistical analysis (t-test) compares densitometry of CCI vs. sham-treatment. * $p<0.01$;  $p<0.001$; * $p<0.00001$.

DETAILED DESCRIPTION OF THE INVENTION

Figure 1:
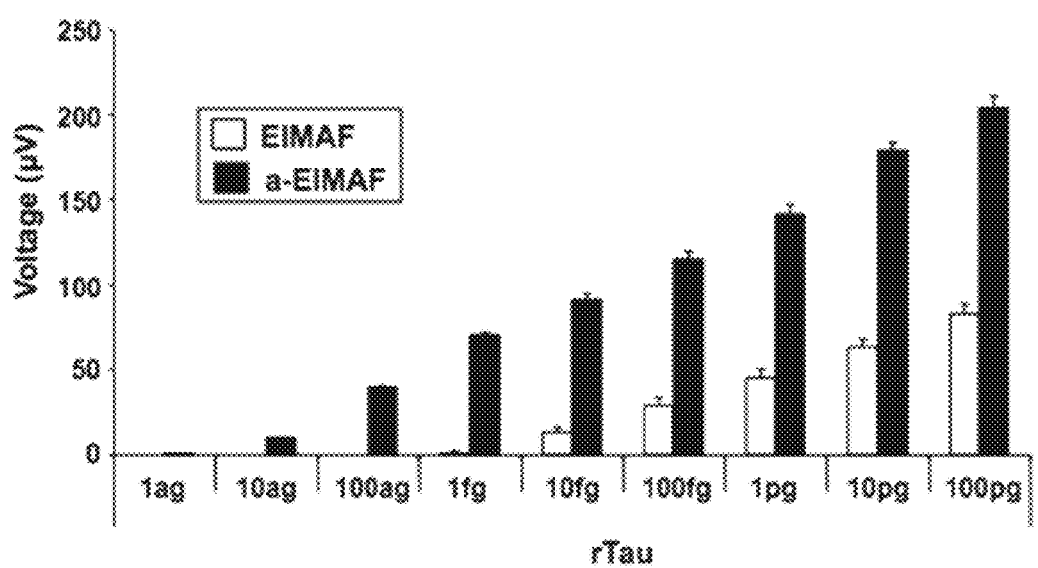
FIG. 1. Sensitivity Limits of EIMAF and a-EIMAF for rTau.

Traumatic brain injury (TBI) is a cause of death and disabilities and can lead to tauopathy-related dementia at an early age. Pathologically, TBI results in axonal injury which is coupled to tau hyperphosphorylation leading to microtubule instability and tau-mediated neurodegeneration. This suggests that the forms of this protein might serve as neuroinjury-related biomarkers for diagnosis of injury severity and prognosis of the neurological damage prior to clinical expression. We initially determined whether we could detect tau in body fluids using a highly sensitive assay. We used a novel immunoassay, EIMAF either alone or in combination with rolling circle amplification (a-EIMAF) for the detection of total (T) and phosphorylated (P) tau proteins from brains and biofluids (blood, CSF) of rodents following controlled cortical impact (CCI) and human patients post sTBI. This assay technology for tau is the most sensitive to date with a detection limit of approximately 100 ag/ml for either T-tau and P-tau. In the rodent models, T-tau and P-tau levels in brain and blood increased following CCI during the acute phase and remained high during the chronic phase (30 days). In human CSF samples, T-tau and P-tau increased during the sampling period (5-6 days). T-tau and P-tau in human serum rose during the acute phase and decreased during the chronic stage but was still detectable beyond 6 months post sTBI. Thus, EIMAF has the potential for both assessing the severity of the proximal injury as well as for prognoses using easily accessible samples.

DEFINITIONS

"Tau-associated disease" as defined herein means diseases associated with abnormalities in Tau as well as diseases that are "tauopathies." The present invention focuses on alterations in tau indicative of severity of traumatic brain injury. Other tau-associated diseases include, but are not limited to, frontotemporal dementia, including the subtype of frontotemporal dementia and Parkinsonism linked to chromosome 17 (FTDP-17), progressive supranuclear palsy, corticobasal degeneration, Pick's disease, agyrophilic grain disease, as well as Parkinson's disease, Down syndrome, post-encephalic Parkinsonism, myotonic dystrophy, Niemann-Pick C disease, dementia pugilistica, Blint disease, prion diseases, amyotrophic lateral sclerosis, Parkinsonism-dementia complex of Guam, multiple sclerosis, glaucoma, diabetic retinopathy, as well as Huntington's disease, Lewy body dementia, Charcot-Marie-Tooth disease, hereditary spastic paraplegia, and multiple system atrophy.

"Tauopathy" as defined herein means a neurodegenerative disease associated with fibrillar forms of Tau protein (tangles) in brain.

Enhanced Immunoassay using Multi-Arrayed Fiberoptics (EIMAF), refers to a highly sensitive immunoassay which when combined with rolling circle amplification is effective to differentiate and quantify total (T) and phosphorylated (P) tau proteins or other biomarkers, from brains and biofluids (e.g., blood, CSF).

The term "reduce" or "reducing" as used herein refers to limit occurrence of the disorder in individuals at risk of developing the disorder.

The term "modulate" as used herein means to regulate, alter, adapt, or adjust to a certain measure or proportion.

The term "disease" or "disorder" as used herein refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

The terms "subject" or "individual" or "patient" are used interchangeably to refer to a member of an animal species of mammalian origin, including humans.

The phrase "a subject having a progressive cognitive disease" as used herein refers to a subject who presents with diagnostic markers and/or symptoms associated with a progressive cognitive disease. A progressive cognitive disease is usually diagnosed clinically from the patient history, collateral history from relatives, and clinical observations, based on the presence of characteristic neurological and neuropsychological features and the absence of alternative conditions. These criteria require that the presence of cognitive impairment, and a suspected dementia syndrome, be confirmed by neuropsychological testing. Advanced medical imaging with computed tomography (CT) or magnetic resonance imaging (MRI), and with single photon emission computed tomography (SPECT) or positron emission tomography (PET) may be used to help exclude other cerebral pathology or subtypes of dementia. Assessment of intellectual functioning including memory testing can further characterize the state of the disease. A histopathologic confirmation including a microscopic examination of brain tissue may be required for a definitive diagnosis. For AD, eight cognitive domains are most commonly impaired: memory, language, perceptual skills, attention, constructive abilities, orientation, problem solving and functional abilities. These domains are equivalent to the NINCDS-ADRDA Alzheimer's Criteria as listed in the Diagnostic and Statistical Manual of Mental Disorders (DSM-IV-TR) published by the American Psychiatric Association (incorporated in its entirety herein by reference).

A subject at risk of having a progressive cognitive disease is one who has one or more predisposing factors to the development of a progressive cognitive disease.

A subject in need thereof is a patient having, or at risk of having, a progressive cognitive disease.

The term "dementia" as used herein refers to a decline or a progressive decline in cognitive function due to damage or disease in the brain beyond what might be expected from normal aging. The term "cognitive function" refers to the intellectual processes resulting in an understanding, perception, or awareness of one's ideas as well as the ability to perform mental tasks, such as thinking, learning, judging, remembering, computing, controlling motor functions, and the like.

The term "phosphorylated tau accumulation modulating amount" as used herein refers to a therapeutically effective amount of a composition that modulates the phosphorylation of tau protein. A phosphorylated tau accumulation-modulating amount includes prophylactic or preventative amounts of the compositions of the described invention.

The following materials and methods are provided to facilitate the practice of the present invention.

Controlled Cortical Impact (CCI)

Brain trauma in rats and mice was produced using an electromagnetic contusion device (Myneurolab, St. Louis, Mo.). Adult male (280-300 g) Sprague-Dawley rats (Harlan: Indianapolis, Ind., USA) or C57Bl/6J mice (~30 gms) (Jackson Labs) were anesthetized with 4% isoflurane in a carrier gas of oxygen (0.8 L/min) and maintained in 2.5% isoflurane as anesthesia in the same carrier gas. Core body temperature was monitored continuously and maintained at 37±1° C. Animals were placed onto a stereotactic apparatus (David Kopf, Tujinga, Calif.) in a prone position and secured by ear and incisor bars. Following a midline cranial incision and reflection of the soft tissues, a unilateral (ipsilateral to site of impact) craniotomy (4 mm and 7 mm diameter for mice and rats, respectively) was performed adjacent to the central suture, midway between bregma and lambda. The dura mater was kept intact over the cortex. Brain trauma was produced by impacting the right (ipsilateral) cortex with an aluminum impactor tip (housed in a pneumatic cylinder) (3.5 mm and 5 mm diameter for mice and rats, respectively) at a impact velocity of 4.5 m/s with a 1.5 mm (mice) or 2.5 mm (rats) depth and 150 ms dwell time. The craniotomy was covered with a plastic plate that was cemented (Grip Cement, Dentsply, York, Pa.) to the skull. Sham-injured control animals were subjected to the same surgical procedures but did not receive the impact injury. Animals were monitored and recovery from anesthesia was confirmed when they regained their ability to right themselves and ambulate. Appropriate pre- and post-injury management was preformed to minimize pain and discomfort and to insure compliance with guidelines set forth by the SUNY Downstate Medical Center Institutional Animal Care and Use Committee (protocol #'s 08-477-10 and 13-10382) and the National Institutes of Health guidelines detailed in the Guide for the Care and Use of Animals.

Brain tissue and blood samples were harvested from mice and rats at selected times after the CCI. At each time point mice and rats were anesthetized with isoflurane before sample collection. Blood was collected in non-heparinized tubes from tail veins or by cardiac exsanguination. Following centrifugation, serum was obtained, stored at −80° C., and diluted (1:20) prior to use. Brains were removed immediately following cervical dislocation and stored at −80° C. In addition to these samples, frozen brains and blood from 8 month old JNPL3 (P301L) and Tau knockout (TauKO) mice were generously supplied by Dr. Karen Duff (Columbia University Medical Center, New York, N.Y.).

Human Samples

Control CSF samples were purchased from Bioreclamation, Inc. Archived TBI CSF samples were also assessed. Samples were derived from 6 patients with blunt trauma to the head, and with a GCS<8, enrolled in a sTBI study where CSF was collected from adult subjects presenting to the Emergency Department of Ben Taub General Hospital, Baylor College of Medicine, (Houston, Tex.). The study protocol was approved by the Baylor College of Medicine (IRB # H-13606). CSF was collected until a ventriculostomy catheter was no longer clinically indicated. CSF samples (10 ml), with a collection time not exceeding 1 hr, were diverted to 15 ml conical polypropylene centrifuge tubes (BD Falcon) and centrifuged at 4,000×g at room temperature for 5 min to remove loose cells and debris. One ml aliquots of the cleared supernatants were pipetted into cryogenic tubes, snap-frozen and stored at −80° C. Archived serum samples from sTBI subjects and non-TBI controls were collected at the University of Pittsburgh Medical Center (IRB #'s PRO08020342, IRB0308021). Enrolled subjects in this cohort also sustained blunt trauma to the head and had an admission GCS<8. Initial blood samples were collected during the acute stage (<3 days post-injury) and also at approximately 1 mo., 3 mo. and 6 mo. post-TBI. Non-TBI control sera were collected only once per subject using similar procedures. After collection, blood samples were allowed to coagulate for 30-60 min at room temperature before centrifugation at 2,500×g for 10 min. Supernatants (serum) were collected, aliquoted, snap-frozen and stored at −80° C. Prior to analysis, serum and CSF were diluted 1:20 and 1:100, respectively.

Human CSF and serum samples were transferred to SUNY Downstate for use in this study with NIH clinical exemption 4 (IRB #00003624) from Federal regulations.

Preparation of Tissue Extracts

Soluble tissue extracts were generated by homogenization of rodent brain tissue in 1×lysis buffer (20 mM Tris-HCl, pH 7.4, 150 mM NaCl, 5 mM EGTA, 5 mM EDTA, 1% Triton X-100, 1 mM Na vanadate, 1 mM dithiothreitol, and 100× Halt protease inhibitor (Fisher Scientific) on ice. Extracts were transferred to 1.5 ml microcentrifuge tubes, microfuged at 10,000×g for 15 min at 4° C. and the supernatants (soluble proteins) were collected and stored at −80° C. until analysis. Protein concentrations were determined using a micro BCA protein assay kit (Fisher Scientific).

EIMAF and a-EIMAF

The anti-tau monoclonal antibodies (Mabs) used were previously described[55] and epitopes are indicated in italics below. For EIMAF coupled to rolling circle amplification (a-EIMAF), high-binding 96-well microtiter plates (Costar) were coated with capture Mab at 6 µg/ml final concentration [Mab DA31 (aa150-190) for T-tau and Mabs CP13 (pSer-202) (rodents samples) or RZ3 (pThr-231) (human samples) for P-tau]. Following an overnight incubation at 40° C., unoccupied binding sites were blocked for 1 hr with casein. A 100 µl aliquot of diluted brain or blood (serum at 1:20 dilution is used to avoid matrix effects) sample was added, incubated and followed by the addition of a biotinylated detection Mab DA9 (aa102-140) (100 µl at 4 µg/ml final Mab concentration).

Five 10 min washes with phosphate-buffered saline containing 0.2% Tween-20 (PBST) were followed with the addition of 100 µl of streptavidin (5 µg/ml) per well and incubation for 1hr at 37° C. A biotinylated prostate-specific DNA primer (5'-TTTTTTTGTCCGTGCTAGAAGGAAA-CAGTTAC-3'; SEQ ID NO: 1) (100 µl at 4 µg/ml) was added for 1 hr at 37° C. Following the addition of a T4-DNA ligase-pretreated prostate DNA template (1 mg/ml), RCA was initiated by adding 100 µl of reaction mixture consisting of: φ29 DNA polymerase reaction buffer, bovine serum albumin, nucleotide triphosphates supplemented with dUTP-Texas Red, and φ29 DNA polymerase.[56] Incubation for several hrs is followed by PBST washes, addition of 1N NaOH, neutralization with 1 M Tris-HCl, pH 7.5, heat treatment (100° C. for 15 min) and fluorescence analysis using surround optical fluorescence detection. For direct, non-amplified detection and relative quantitation of tau, EIMAF was performed as detailed previously and briefly described here.[50] For direct EIMAF, tissue homogenates or biofluids were added to the capture Ab followed by the biotinylated detection Mab DA9. Following a 1 hr incubation, streptavidin conjugated to Rhodamine Red X (1:1000) (Invitrogen) was added and incubated for 1 hr. The wells were washed with TBS containing Tween-20, treated with NaOH and neutralized. A 90 µl sample was drawn up into a 100 µl Microcap (Drummond Scientific) micro-capillary tube which was then inserted into a specifically designed tube sample holder for laser excitation and emission quantitation. Each EIMAF and a-EIMAF sample was tested in triplicate and, depending on available sample volumes, duplicated in independent experiments. Although we have found that a-EIMAF is not required for all serum samples, it is required for many of them. Therefore our standard protocol is to assay all non-CNS samples directly by a-EIMAF.

Immunoblotting and ELISA

For capture enzyme-linked immunosorbent assay (ELISA), 96-well microtiter plates were coated with 100 µl of purified capture antibody (Mab DA31 for T-tau, Mab CP13 for rodent P-tau, Mab RZ3 for human P-tau) at a concentration of 5 µg/ml in PBS. After overnight incubation at 4° C. the wells were washed 2× with PBST and blocked by adding 200 µl 1% non-fat dry milk in PBS, pH 7.4. A 100 µl aliquot of PBS-diluted antigen was incubated at 37° C. for 1 hr followed by 4 washes with PBST. Biotinylated DA9 (100 µl at 1 µg/ml) was added and incubated for 1 hr at room temperature (RT). Wells were washed 4 times with PBST followed by the addition of 100 µl of streptavidin conjugated to alkaline phosphatase and incubation at RT for 60 min. This was followed by the addition of 100 µl PNPP substrate, incubation at 37° C. for 60 min and optical density readings at 405 nm.

For immunoblotting analysis, soluble protein fractions (25 µg per lane) from the brain tissue extracts were separated using SDS-PAGE (10% resolving gels). Equivalent sample volumes were loaded on each lane. Proteins were electrotransferred to nitrocellulose membranes and the blots were blocked using 5% non-fat dry milk in PBST for 30 min at RT. Blots were incubated with primary Ab (1:1000 dilution of Mab DA9 conditioned media for T-tau and Mab CP13 for P-tau) for 2 hrs at 37° C., washed 3× in PBST (15 min each) followed by goat anti-mouse IgG (Fab specific) conjugated with alkaline phosphatase (1:2000) (Sigma) in 1% non-fat dry milk—PBST for 2 hrs. Following 3 PBST washes (15 min each), the blots were developed in substrate buffer (100 mM Tris-HCl, pH 9.5, 100 mM NaCl, and 5 mM $MgCl_2$) containing NBT (0.33 mg/ml)-BCIP (0.165 mg/ml). All data shown are representative of three separate experiments. Quantification of tau proteins was performed by densitometric analysis using NIH Image J software. All data shown are representative of multiple independent experiments.

The following example is provided to illustrate certain embodiments of the invention. It is not intended to limit the invention in any way.

EXAMPLE I

Here we report the use of EIMAF with and without pre-assay target amplification, for T-tau and P-tau detection in both rodent and human CNS tissue and/or biofluid samples (blood, CSF) following sTBI. Based on these findings from rodent TBI models and clinical samples obtained from individuals with TBI, we believe that the EIMAF technology for determining T-tau and P-tau levels provide the degree of sensitivity needed for assessing tau levels as a prognostic biomarker for patient recovery and/or development or progression of a tauopathy.

Figure 2A:
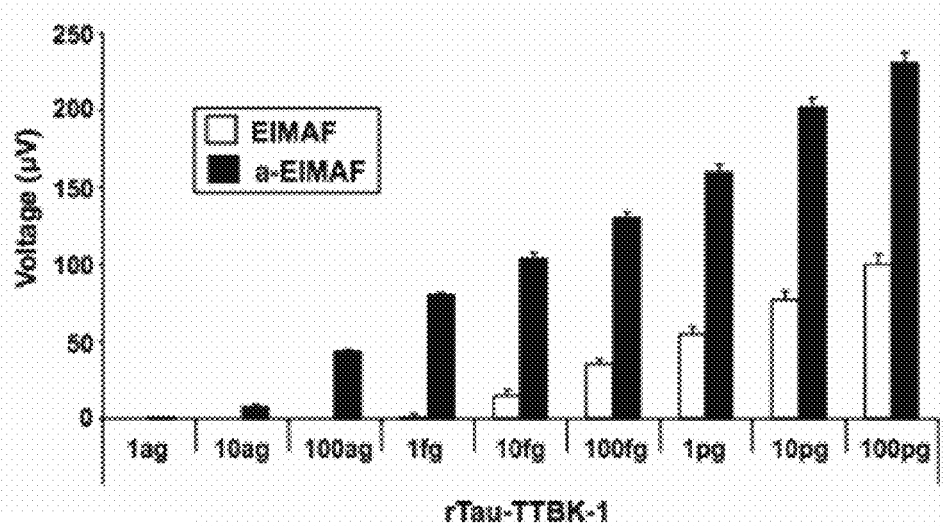
FIGS. 2A and 2B. Sensitivity Limits of EIMAF and a-EIMAF for P-Tau using rTau-TTBK-1 with Mab CP13 (FIG. 2A) and rTau-GSK3β with Mab RZ3 (FIG. 2B).
Figure 2B:
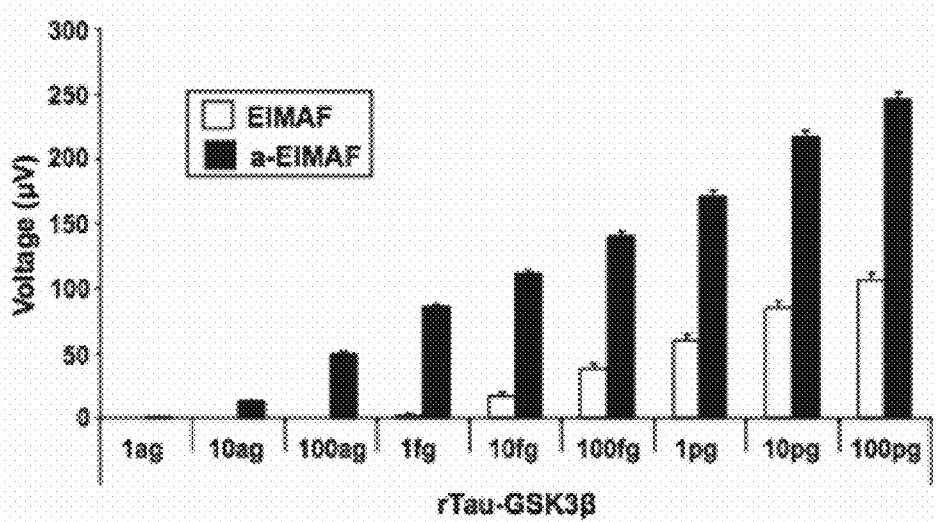

The sensitivity of EIMAF for the detection of T-tau was determined by performing assays on serial dilutions of recombinant human Tau-441 (rTau) (EMD Millipore, Billerica, Mass.) (FIG. 1). Measuring rTau without pre-assay signal amplification by RCA, we reliably and repeatedly detected rTau down to <100 fg/ml. However, using RCA to increase the target signal detected by EIMAF (i.e. a-EIMAF) assay sensitivity was increased by approximately 3 logs to <100 ag/ml. The data presented in this figure was also used as a standard curve for quantifying T-tau levels in the experimental samples being assayed to calibrate the voltage readings expressed by EIMAF and a-EIMAF. To our knowledge, this is the most sensitive assay for T-tau detection to date. Similarly, for studies on EIMAF and a-EIMAF, sensitivity and dynamic range were determined for P-tau using, as a surrogate target, rTau phosphorylated by either TTBK-1 (FIG. 2a) or GSK-3β (FIG. 2b) (SignalChem, Richmond, BC). TTBK-1, a serine/threonine/tyrosine kinase belonging to the casein kinase 1 superfamily, phosphorylates at AD-related sites (Ser-198, Ser-199, Ser-202 and Ser-422) and is also associated with tau aggregation.[30] GSK-3β is a physiological serine/threonine kinase for tau that targets numerous tau phosphorylation sites identified in NFT and other tau-positive inclusions. Phosphorylation of tau at Thr-231 by GSK-3β lays a critical role in regulating the ability of tau to bind to and stabilize microtubules. In addition, Rankin et al.[57] reported that the major sites phosphorylated by GSK-3β include Thr-205, Ser-214, Thr-231, Ser-262, Ser-356, Ser-400, Ser-404, and Ser-409. Our results support these findings in that we found CP13 (pSer-202) had greater reactivity for rTau-TTBK-1 than for rTau-GSK-3β, and, conversely, RZ3 (pThr-231) had greater reactivity for rTau-GSK-3β than for rTau-TTBK-1 (data not shown). Accordingly, we focused our efforts only on the more highly reactive combinations. The sensitivity and dynamic range of EIMAF and a-EIMAF for P-tau detection with CP13 (using rTau-TTBK-1) (FIG. 2a) and RZ3 (using rTau-GSK-3β) (FIG. 2b) are similar to the results obtained for T-tau detection using rTau (FIG. 1) and includes the approximate 3 log increase in detection with EIMAF following amplification.

We compared the sensitivity of EIMAF to sandwich ELISA (FIG. 3) using, as a source of T-tau and P-tau, serial 10-fold dilutions ($10^{-4}$-$10^{-12}$) of brain lysates from 8 month old JNPL3 (P301L) mice which exhibit extensive tauopathy and TauKO mice as negative controls.[58, 59] As anticipated, T-tau and P-tau were not detected in brain homogenates from TauKO mice by either sandwich ELISA or EIMAF demonstrating the high specificity of these immunoassays (FIG. 3). Both T-tau and P-tau were readily detectable by both sandwich ELISA and EIMAF. Both T-tau and P-tau were detected in the $10^{-4}$ dilution by sandwich ELISA, but not at $10^{-5}$ and $10^{-6}$ dilutions of T-tau and P-tau, respectively. In contrast, a different profile was observed when EIMAF was used for T-tau and P-tau detection of the same brain lysates (FIG. 3). Detection of T-tau and P-tau by EIMAF in JNPL3 (P301L) brain remained constant from a $10^{-4}$ to $10^{-8}$ brain lysate dilution for P-tau and to a $10^{-9}$ brain lysate dilution for T-tau. P-tau and T-tau were not detected by EIMAF at a $10^{-11}$ and $10^{-12}$ brain lysate dilution, respectively. Taken together, these studies demonstrate that EIMAF has a sensitivity that is approximately 5-6 logs greater than sandwich ELISA with an additional ~3 logs when a-EIMAF is used.

To further assess assay utilization, sensitivity and specificity, we compared the detection of T-tau in serum from 8 month old P301L mice and TauKO mice (data not shown). Using a 1:20 serum dilution, T-tau from P301L mice was readily detectable by a-EIMAF but not by sandwich ELISA or EIMAF alone. As expected, diluted serum from TauKO mice gave readings similar to PBS background controls for all three assays. These studies demonstrate the utility of a-EIMAF for biomarker detection when the concentration of the analyte is too low for detection by conventional assays.

Using a-EIMAF we monitored the levels of T-tau and P-tau in rat serum over a 30 day time period post-CCI (FIG. 4). At each time point, serum was collected from separate groups each consisting of 5 rats and serum samples were analyzed individually. We observed that there was a baseline level of T-tau even in naïve rat serum. The levels of T-tau began to increase gradually by day 2 and continued until day 3 after which it remained constant for the remainder of the time course. In contrast, P-tau levels were very low in naïve rat serum and there was a dramatic increase from baseline by day 3 post-CCI that continued on an upward trend until day 30.

Figure 5:
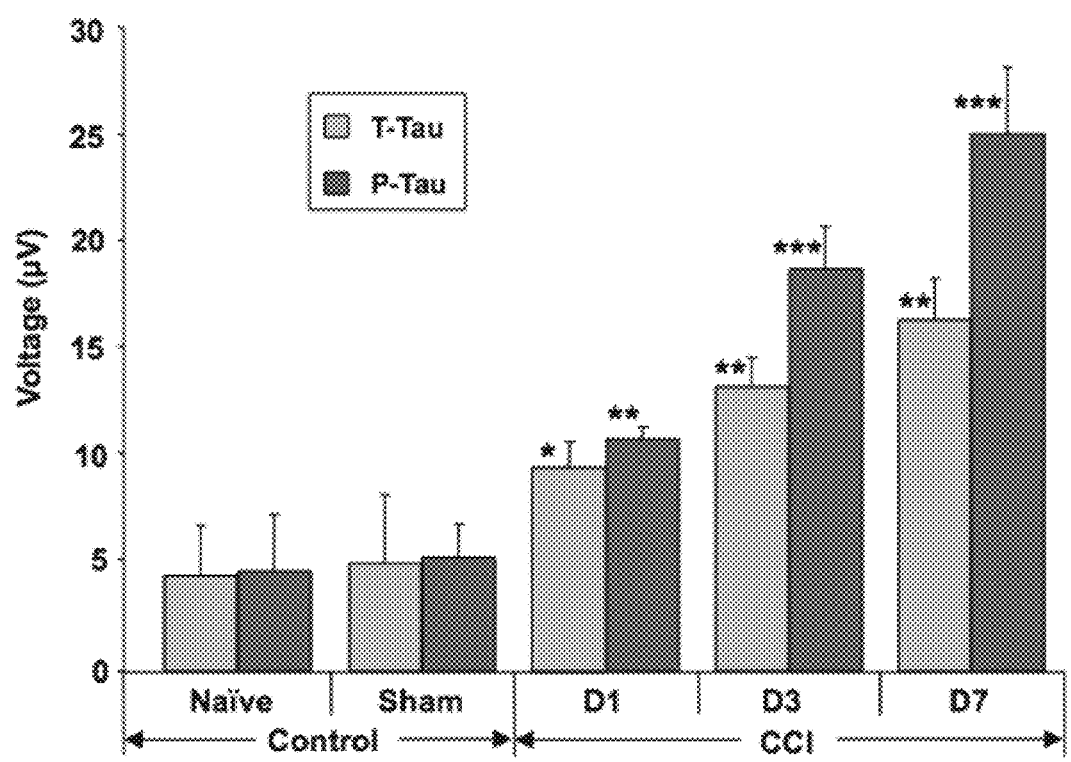

Mice were also subjected to CCI and followed by a-EIMAF over a 7 day period during which changes in serum levels of T-tau and P-tau were determined (FIG. 5). The controls (naive, sham) and CCI groups each consisted of 5 mice. At each time point blood was collected, processed and analyzed individually from each mouse prior to sacrifice. In contrast to the rat model, the T-tau levels in mouse serum increased at day 1 post-CCI, the first time point selected, and showed continued increases at days 3 and 7 in comparison to sham mice. Only values for day 1 sham mice are plotted in FIG. 5 since the values in sham mice at days 1, 3 and 7 were all very similar. In the CCI group, P-tau levels also followed the same profile increasing continuously from day 1 to day 7 (all statistically significant when compared to day 1 sham). However, the increases in P-tau were more dramatic than T-tau over the 7 day period. Although it is currently unclear why P-tau levels showed a greater increase than T-tau in mice, this may be due to a difference in epitope accessibility with the P-tau epitope being more detectable in serum. However, this does not seem to be an issue with the rat model study described above (FIG. 5).

To try to address this issue found in serum, Western blotting for T-tau and P-tau was performed on the mouse brain lysates (FIG. 6). Since western blotting was performed on denatured proteins, the influence of tau conformation is eliminated. The immunoblotting data demonstrated that following CCI, increases in T-tau levels continued from day 1 to day 7 while increases in P-tau followed the T-tau increase and were observed at days 3 and 7. However, P-tau levels did not exceed T-tau levels at any time point. Taken together, these results suggest that the discrepancy in data for the non-denatured T-tau and P-tau in murine serum described above (FIG. 5) is likely due to conformational differences resulting in altered epitope availability.

Figure 7A:
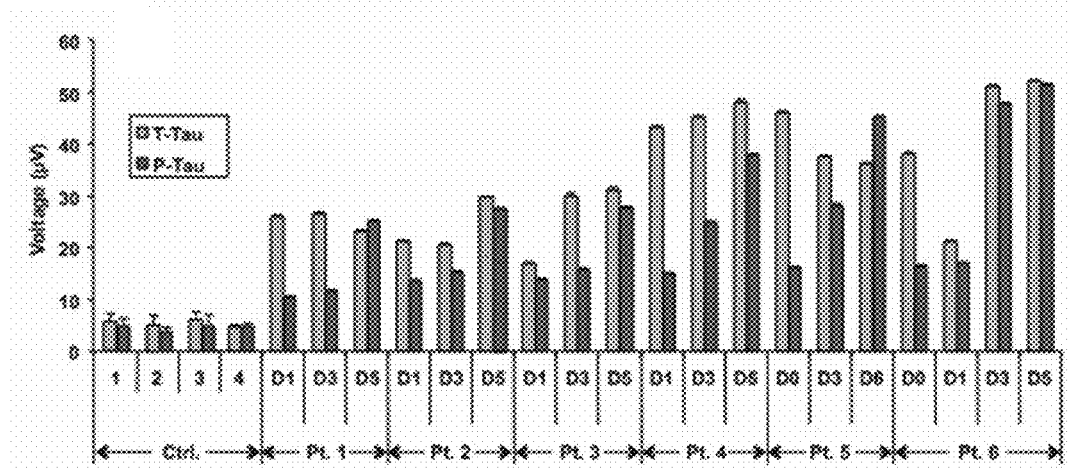
FIGS. 7A-7B. Detection of T-Tau and P-Tau in human CSF (1:100 dilution) during the acute and chronic phases post sTBI using EIMAF (FIG. 7A) and ELISA (FIG. 7B).
Figure 7B:
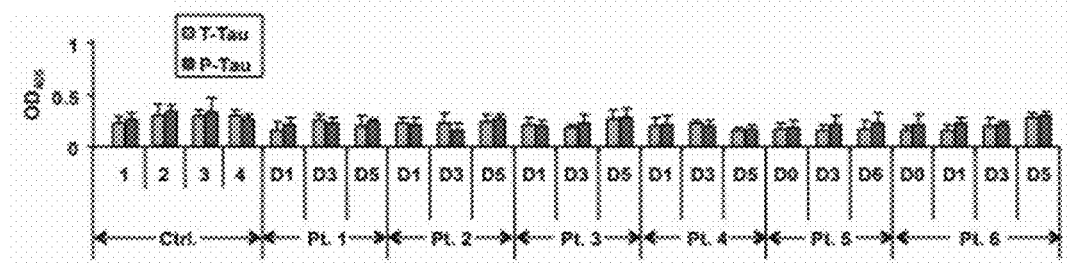

As a next step, the utility of EIMAF for detection of tau in human biofluids was investigated. First, timed acute phase human CSF samples collected from 6 sTBI patients were analyzed. T-tau and P-tau levels in diluted (1:100) CSF samples were measured using EIMAF or sandwich ELISA for comparison (FIG. 7). While T-tau and P-tau were readily detectable in the human CSF samples using EIMAF (FIG. 7A), sandwich ELISA (FIG. 7B) lacked the requisite sensitivity. FIG. 7 presents the data obtained using serial CSF samples from 6 sTBI subjects extending from days 0-6 after injury, in comparison with 4 non-TBI control CSF samples. In all 6 sTBI subjects, the T-tau and P-tau levels in the first available sample were higher than in the non-TBI controls (FIG. 7A). Interestingly, CSF T-tau levels either remained unchanged or rose during this time course with T-tau concentrations ranging from 13.3-20.2 ng/ml exemplifying patient to patient variability. On the other hand, CSF P-tau levels for all 6 sTBI subjects exhibited an increase over the time course examined, from the first sample on day 0 or 1 until the last sample collected on day 5 or 6 (FIG. 7A) with the range of P-tau concentrations 7.1-19.8 ng/ml.

Figure 8:
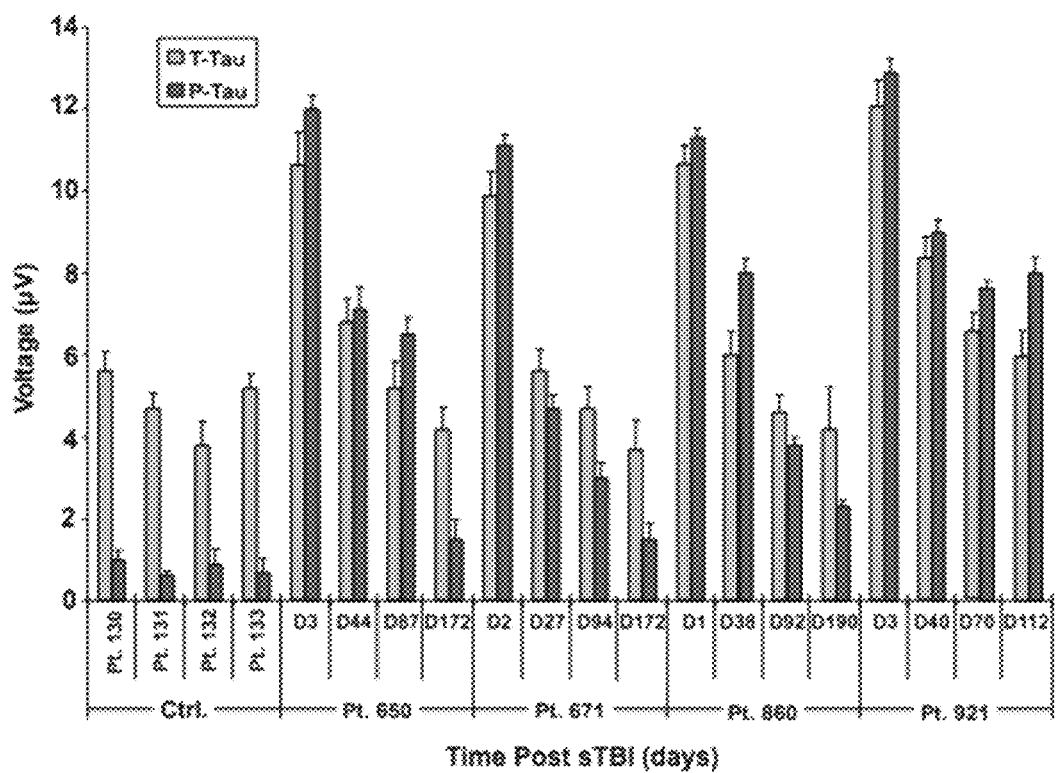
FIG. 8. Detection of T-Tau and P-Tau in human serum post sTBI by a-EIMAF. Human serum samples were diluted 1:20 in PBS and assayed by a-EIMAF for T-Tau (Mab DA31) and P-Tau (Mab RZ3) in combination with biotinylated Mab DA9 for detection. Serum levels of both T-Tau and P-Tau are elevated in the acute phase (range D1-D3) in comparison to control serum. In the chronic serum samples (range D27-D190), the majority of T-Tau returned to control levels. In contrast, P-Tau levels in most sTBI serum samples remained higher than control levels.

We next analyzed tau levels in a series of human serum samples taken from 4 sTBI patients (Pts. 650, 671, 860, 921) during either the acute stage (≤3 days) or at three time points more remote from injury (≥21 days: approximately at 1, 3, 6 mo. post-TBI) (FIG. 8). In a group of non-TBI control subjects (Pts. 130-133), serum T-tau levels were about 3-4 fold higher than P-tau levels (~144-158 fg/ml T-tau vs ~38-40 fg/ml P-tau). For sTBI subjects, although the actual T-tau and P-tau levels varied between the patients, the data profiles from each of the 4 patients produced similar findings: (i) serum levels of T-tau and P-tau during the acute phase (first serum samples day 1-3) post-TBI rose dramatically (~375-405 fg/ml T-tau; ~380-410 fg/ml P-tau) compared to the levels in the non-TBI control sera, (ii) P-tau levels became comparable to the T-tau levels in the samples during the acute phase of TBI, and (iii) during the chronic stage (approximately 1, 3 and 6 mo. post-injury), the T-tau and P-tau levels declined steadily at similar, but not identical rates for 2 of the patients (Pts. 671, 860), slower for Pt. 650 and slowest for Pt. 921 (FIG. 8). Of note, even at the more remote stage (approximately 3 and 6 mo. post-injury), T-tau, and importantly P-tau, levels are still detectable in serum using a-EIMAF and remain significantly higher than the control values.

In additional studies, plasma samples were obtained from the multi-center, multi-year NIH funded project know as the "Transforming Research and Clinical Knowledge in Traumatic Brain Injury" (TRACK-TBI). Approximately 80% of the TRACK-TBI patients were subjected to mild to moderate TBI with the remainder having severe TBI. These 65 plasma samples were divided into the following four groups: 1. controls, no TBI, 2. acute TBI, <24 hrs post neuroinjury, negative CT scans, 3. acute TBI, <24 hrs. post neuroinjury, positive CT scans, 4. chronic patients, average time post injury was 5.9 months.

Figure 9:
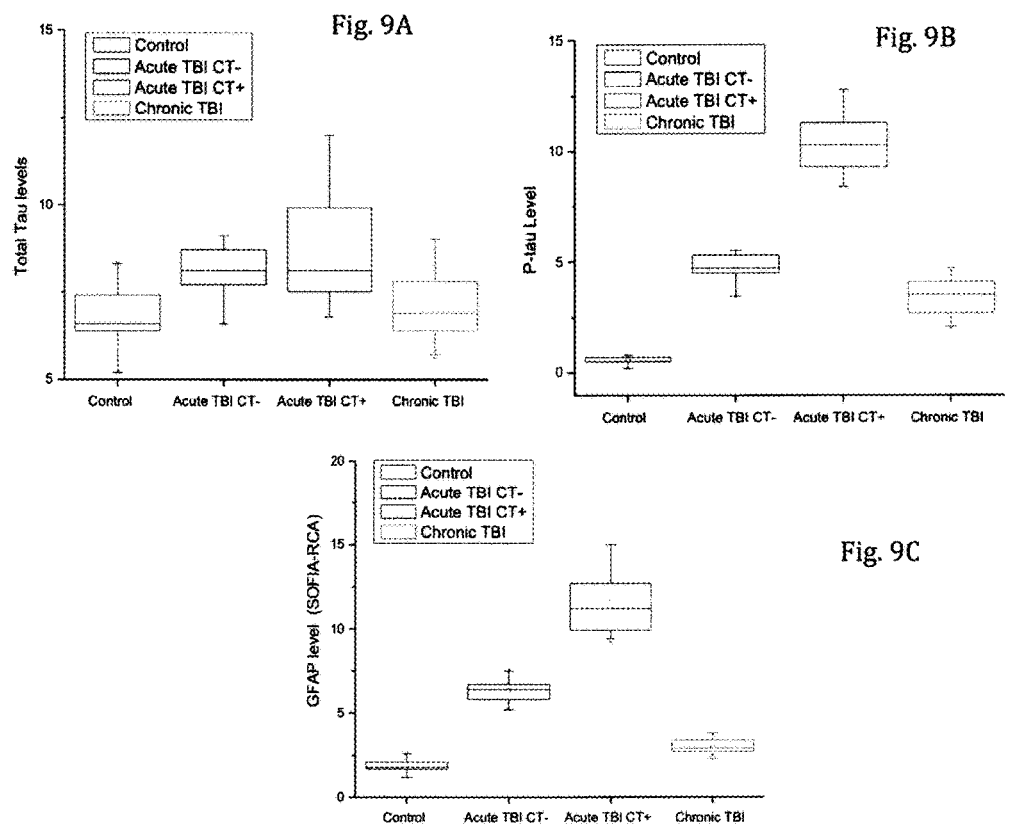
FIGS. 9A-9C. EIMAF for detection of Total Tau (T-Tau), P-Tau and GFAP using plasma from TRACK-TBI study which covers the spectrum of mild-moderate to severe TBI. Plasma was diluted (1:100) from a total of 65 patients and assayed by a-EIMAF. In the acute phase of TBI (24 hr.), T-Tau (FIG. 9A), P-Tau (FIG. 9B) and GFAP (FIG. 9C) in TBI (CT negative) are all higher than normal control, while TBI (CT positive) values are yet higher. In chronic patients (avg. 5.9 mo. post-TBI) GFAP and T-Tau levels are approaching those of normal, yet P-Tau remains still higher. (For TRACK-TBI study reference see Okonkwo et al., 2013; Diaz-Arrastia et al., 2013).

All plasma samples were diluted 1:100 followed by utilization of a-EIMAF to analyze the biomarkers T-Tau (A), P-Tau (B) and glial fibrillary acidic protein (GFAP) (C). The plasma levels of T-Tau, P-Tau and GFAP from all acute TBI patients were greater than the control plasma samples with the samples from CT positive patients being still higher. Importantly, although the levels of T-Tau and GFAP in plasma from chronic patients declined and approached the values from the control patient plasma as expected, the levels of P-Tau continued to remain higher (FIG. 9). These findings further support the utility of biomarker detection in blood by a-EIMAF for the diagnosis and prognosis of TBI patients.

Discussion

In many instances, surviving TBI victims experience cognitive dysfunction throughout their life coupled with a diminished quality of life. The initial impact from TBI results in many cellular and biochemical changes which exemplifies the complex pathophysiology, resulting in a disease process which increases and prolongs injury severity. The epidemiologic evidence implicates TBI as a probable risk factor for AD. This implies that TBI can initiate mechanistic events leading to neurodegenerative changes. Axonal injury, observed in many sTBI patients, results in accumulation of Aβ peptides and NFTs whose main component is the hyper-phosphorylated, insoluble and filamentous P-tau.[60-64]

Tau inclusions are composed of aggregated tau protein that is abnormally phosphorylated and/or hyper-phosphorylated. Aggregated tau is resistant to dephosphorylation and the extent of tau aggregation corresponds to the degree of neuronal loss and neuron toxicity. Furthermore, hyper-phosphorylated tau is resistant to proteolysis, fails to bind to microtubules and accumulates in neurons resulting in tau toxicity. Neurodegenerative disorders with tau inclusions within both glial and neuronal cell types are referred to as tauopathies.[65] In addition to AD, these include: frontotemporal lobar degeneration, progressive supranuclear palsy, Pick's disease, some prion diseases; amyotrophic lateral sclerosis/parkinsonism-dementia complex; CTE; and some genetic forms of Parkinson's disease.[65-68] The fact that the tau inclusions are localized in the brain regions whose functions are compromised suggests that these inclusions are partially responsible for the neuropathogenesis of these disorders. This is strengthened by studies demonstrating that progression and duration of AD is correlated with NFT formation.[69, 70]

In the present example, we describe, an ultrasensitive immunoassay technology (EIMAF) and its modification (a-EIMAF) that, for the first time, documents changes in T-tau and P-tau in two rodent models and human biofluid samples following sTBI. We have found that serum T-tau and P-tau levels generally increase during the acute stage of sTBI in rodent serum (from days 2 to 30 for T-tau and from days 3 to 7 for P-tau in rats and days 1 through 7 in mice) (FIG. 4, 5). During the subacute/chronic state (days 14-30), the increased levels of both T-tau and P-tau are maintained in the rat model (FIG. 4). In studies on human biofluid samples following sTBI, the elevated T-tau levels are generally sustained while elevated P-tau levels actually increased during the acute stage of sTBI (days 0 to 6 post-injury) in human CSF (FIG. 8). Furthermore, in human TBI, the serum samples from the acute phase of injury have the most elevated T-tau and P-tau levels (FIG. 8, 9). However, T-tau levels appear to return to normal by about 1 mo. post-injury, while P-tau levels, though reduced, are still substantially higher than control levels even at 6 mo. post-injury (FIG. 9).

NFTs and CSF tau are commonly increased by a factor of 3-4 in AD.[22, 26, 27] Following TBI, not only do the tau levels in the CSF increase, but changes of tau levels in the serum suggests its use as a specific serum biomarker in humans and experimental models.[35, 36, 49, 71] Analysis of rat serum T-tau protein following TBI demonstrated that although tau levels in serum increased as a function of severity and time at 1 and 6 hrs after TBI, the serum T-tau may not be suitable as a marker 24 hr after injury.[49] Consistent with the increase in T-tau, additional reports analyzing the biomarkers cleaved (c)-tau,[48] S-100β and neuron specific enolase (NSE),[72, 73] also reported increased levels within 6 hr after TBI in rats. The levels of brain biomarkers found in serum is influenced by the integrity of the blood-brain barrier (BBB) integrity and 6 hrs after TBI the integrity of BBB would re-established resulting in a decrease in the serum tau levels.[48] We did not observe a similar time course profile for serum T-tau and P-tau in our studies.

Evaluating the neurological damage that results from TBI is a continuing challenge. Techniques used to assess brain trauma include neuropsychological assessments and neuroimaging which are partially subjective when interpreting the data. The use of biochemical methods for the detection of protein biomarkers can offer a more objective analysis of brain injury and be a valuable asset. For example, the capability of detecting biomarkers in biofluids such as blood or urine for evaluating the extent of brain damage presents a less stressful and minimally invasive procedure with reduced costs. Not only can the extent of injury be determined, but these same protein biomarkers may also be useful for monitoring the effectiveness of therapeutic interventions. In addition, the detection and analysis of protein biomarkers would complement the more subjective GCS score that may not be accurate in certain individuals, such as children. Some of the protein biomarkers that have been used are S100β, NSE, glial fibrillary acidic protein (and its breakdown products), ubiquitin carboxyl-terminal esterase L1 and c-tau.[18, 74-82] However, there are issues in the use of these proteins for assessing TBI which includes: sensitivity and specificity, use in adult vs. pediatric patients, lack of correlation between the values in blood and CSF, and lack of correlation with the different levels of TBI severity.

In a recent study the concentrations of plasma T-tau and serum S-100B and NSE were determined in professional ice hockey players who suffered from concussions during the game.[71] The goal of this study was to determine whether blood biomarkers could be used as a guide for acute diagnosis of concussion and injury recovery. Only T-tau was found to be significantly higher in the post-concussive player samples compared with pre-season samples in spite of the high degree of overlap in the range of T-tau values between the two sample groups. T-tau exhibited a biphasic increase following injury and had the greatest diagnostic accuracy when correlated with post-concussive symptoms over time. Further, the T-tau levels were highest during the first hour after concussion, which is similar to our results, but the actual T-tau levels reported (1-100 pg/ml) were greater than those of our study. Whether this is due to the differences in the samples analyzed, assay platform or reagents used is not clear. The levels of S-100B and NSE increased after a game in which no concussion occurred, but T-tau levels were unaffected. Previous studies on serum tau levels after mild or sTBI reported a high degree of variability in the serum tau levels of patients using a sandwich ELISA platform.[15, 35]

Epidemiological evidence, which includes the appearance of fibrillary Aβ plaques in the brain several years following a single sTBI, suggests that TBI may be an risk factor for the development of AD and may accelerate the pathophysiological processes leading to AD.[3, 7-9, 83] Although there exists a causal connection, there are clinical and histopathological differences between AD and TBI,[8] including the distribution of P-tau immunoreactive NFTs, suggesting that the neurophysiological and neuropathological mechanisms leading to the increased risk for neurodegenerative diseases following TBI are highly complex.

Tau pathology and NFTs were also observed in patients who suffered a single sTBI 1-47 years previously.[84] The process of delayed NFT formation in human TBI remains to be explained. Immediately following sTBI, T-tau and P-tau were found to accumulate in both neuronal cell bodies and axons although without clear NFT pathology.[85, 86] In addition, NFTs were not found in TBI patients who died within 4 weeks of injury,[85] suggesting that the mechanisms leading to NFT and/or CTE pathology requires a prolonged time post-injury to develop.

CTE is a clinical entity consisting of tau pathology, in particular the accumulation of NFTs, in the brains of athletes who have been involved in contact sports (professional boxers, American football or ice hockey players, wrestlers) and who sustained several concussions during their career.[37-42] Symptoms of CTE include memory loss, Parkinson-like movements, and dementia.[38, 41, 43-45] In CTE, the vast majority of cases display extensive NFTs while Aβ pathology is much less frequently observed.[42]

Although repeated concussions/mild TBI should be regarded very seriously, the number of individuals examined is still low and the incidence of CTE, its risk factors, and the contribution of injury severity (mild/moderate/severe) and number of impacts has yet to be fully characterized.

In conclusion, we have developed tau-specific assay conditions that, in combination with the EIMAF technology, provides the sensitivity required to use the tau protein as a biomarker. In both experimental animal models and human samples the tau protein was detectable in CSF and blood following neurotrauma.

1. Chiu, W. T., Huang, S. J., Tsai, S. H., Lin, J-W., Tsai, M-D., and Lin, T-J. (2007). The impact of time, legislation, and geography on the epidemiology of traumatic brain injury. J. Clin. Neurosci. 14, 930-935.
2. Clinton, J., Ambler, M. W., and Roberts, G. W. (1991). Post-traumatic Alzheimer's disease: preponderance of a single plaque type. Neuropathol Appl Neurobiol 17, 69-74.
3. Mortimer, J. A., Van Duijn, C. M., Chandra, V., Fratiglioni, L., Graves, A. B., Heyman, A., Jorm, A. F., Kokmen, E., Rocca, W. A., Shalat, S. L., Soininen, H., and Hofman, A. (1991). Head trauma as a risk factor for Alzheimer's disease: a collaborative re-analysis of case-control studies. EURODEM Risk Factors Research Group. Int. J Epidemiol 20, S28-S35.
4. Breteler, M. M., Claus, J. J., Van Duijn, C. M., Launer, L. J., and Hofman, A. (1992). Epidemiology of Alzheimer's disease. Epidemiol Rev 14, 59-82.
5. Mayeux, R., Ottman, R., Tang, M. X., Noboa-Bauza, L., Marder, K., Gurland, B., and Stem, Y. (1993). Genetic susceptibility and head injury as risk factors for Alzheimer's disease among community-dwelling elderly persons and their first-degree relatives. Ann Neurol 33, 494-501.
6. Guo, Z., Cupples, L. A., Kurz, A., Auerbach, S. H., Volicer, L., Chui, H., Green, R. C., Sadovnick, A. D., Duara, R., DeCarll, C., Johnson, K., Go, R. C., Growdon, J. H., Haines, J. L., Kukull, W. A., and Farrer, L. A. (2000). Head injury and the risk of AD in the MIRAGE study. Neurology 54, 1316-1323.
7. Plassman, B. L., Havlik, R. J., Steffens, D. C., Helms, M. J., Newman, T. N., Drosdick, D., Philips, C., Gau, B. A., Welsh-Bohmer, K. A., Burke, J. R., Guralnik, J., and Breitner, J. C. S. (2000). Documented head injury in early adulthood and risk of Alzheimer's disease and other dementias. Neurology 55, 1158-1166.
8. Johnson, V. E., Stewart, W., and Smith, D. H. (2010). Traumatic brain injury and amyloid-beta pathology: a link to Alzheimer's disease? Nat Rev Neurosci 11, 361-370.
9. Magnoni, S., and Brody, D. L. (2010). New perspectives on amyloid-beta dynamics after acute brain injury: moving between experimental approaches and studies in the human brain. Arch Neurol 67, 1068-1073.
10. Li, L. M., Menon, D. K., and Janowitz, T. (2014). Cross-sectional analysis of data from the U.S. clinical trials database reveals poor translational clinical trial effort for traumatic brain injury, compared with stroke. PLoS One 9: e84336. doi: 10.1371/journal.pone.0084336.
11. Raabe, A., Grolms, C., Sorge, O., Zimmermann, M., and Seifert, V., 1999. Serum S-100B protein in severe head injury. Neurosurgery 45, 477-483.
12. Woertgen, C., Rothoerl, R., Metz, C., and Brawanski, A. (1999). Comparison of clinical, radiologic, and serum marker as prognostic factors after severe head injury. J Trauma 47, 1126-1130.

13. Franz, G., Beer, R., Kampfl, A., Engelhardt, K., Schmutzhard, E., Ulmer, H., and Delsenhammer, F. (2003). Amyloid beta 1-42 and tau in cerebrospinal fluid after severe traumatic brain injury. Neurology 60, 1457-1461.
14. Vos, P. E., Lamers, K. J., Hendriks, J. C., van Haaren, M., Beems, T., Zimmerman, C., van Geel, W., de Reus, H., Blert, J., and Verbeek, M. M. (2004). Glial and neuronal proteins in serum predict outcome after severe traumatic brain injury. Neurology 62, 1303-1310.
15. Bulut, M., Koksal, O., Dogan, S., Bolca, N., Ozguc, H., Korfali, E., Ilcolet, Y. O., and Parkiak, M. (2006). Tau protein as a serum marker of brain damage in mild traumatic brain injury: preliminary results. Adv. Ther. 23, 12-22.
16. Kavalci, C., Pekdemir, M., Durukan, P., Ilhan, N., Yildiz, M., Serhatlioglu, S., and Seckin, D. (2007). The value of serum tau protein for the diagnosis of intracranial injury in minor head trauma. Am J Emerg Med 25, 391-395.
17. Korfias, S., Stranjalis, G., Boviatsis, E., Psachoulia, C., Jullien, G., Gregson, B., Mendelow, A. D., and Sakas, D. E. (2007). Serum 5-100B protein monitoring in patients with severe traumatic brain injury. Intensive Care Med 33, 255-260.
18. Papa, L., Akinyi, L., Liu, M. C., Pineda, J. A., Tepas, J. J., III, Oli, M. W., Zheng, W., Robinson, G., Robicsek, S. A., Gabrielli, A., Heaton, S. C., Hannay, H. J., Demery, J. A., Brophy, G. M., Layon, J., Robertson, C., Hayes, R. L., and Wang, K. K. W. (2010). Ubiquitin C-terminal hydrolase is a novel biomarker in humans for severe traumatic brain injury. Crit Care Med 38, 138-144.
19. Mondello, S., Robicsek, S. A., Gabrielli, A., Brophy, G. M., Papa, L., Tepas, J., Robertson, C., Buki, A., Scharf, D., Jixiang, M., Akinyi, L., Muller, U., Wang, K. K. W., and Hayes, R. L. (2010). AlphaII-spectrin breakdown products (SBDPs): diagnosis and outcome in severe traumatic brain injury patients. J Neurotrauma 27, 1203-1213.
20. Mondello, S., Jeromin, A., Buki, A., Bullock, R., Czeiter, E., Kovacs, N., Barzo, P., Schmid, K., Tortella, F., Wang, K. K., and Hayes, R. L. (2012). Glial neuronal ratio: a novel index for differentiating injury type in patients with severe traumatic brain injury. J Neurotrauma 29, 1096-1104.
21. Trojanowski, J. Q., Schuck, T., Schmidt, M. L., and Lee, V. M. (1989). Distribution of tau proteins in the normal human central and peripheral nervous system. J Histochem Cytochem 37, 209-215.
22. Sivanandam, T. M., and Thakur, M. K. (2012). Traumatic brain injury: a risk factor for Alzheimer's disease. Neurosci Biobehav Rev 36, 1376-1381.
23. Alonso, A., Zaidi, T., Novak, M., Grundke-Iqbal, I., and Iqbal, K. (2001). Hyperphosphorylation induces self-assembly of tau into tangles of paired helical filaments/straight filaments. Proc Natl Acad Sci USA 98, 6923-6928.
24. Feijoo, C., Campbell, D. G., Jakes, R., Goedert, M. and Cuenda, A. (2005). Evidence that phosphorylation of the microtubule-associated protein Tau by SAPK4/p38delta at Thr50 promotes microtubule assembly. J Cell Sci 118, 397-408.
25. Morris, M., Maeda, S., Vossel, K., and Mucke, L. (2011). The many faces of tau. Neuron 70, 410-426.
26. Blennow, K., and Hampel, H. (2003). CSF markers for incipient Alzheimer's disease. Lancet Neurol 2, 605-613.
27. Selkoe, D. J., and Schenk, D. (2003). Alzheimer's disease: molecular understanding predicts amyloid-based therapeutics. Ann Rev Pharmacol Toxicol 43, 545-584.
28. Goedert, M., Jakes, R., Crowther, R. A., Cohen, P., Vanmechelen, E., Vandermeeren, M., and Cras, P. (1994). Epitope mapping of monoclonal antibodies to the paired helical filaments of Alzheimer's disease: identification of phosphorylation sites in tau protein. Biochem J 301, 871-877.
29. Davies, P., 2000. Characterization and Use of Monoclonal Antibodies to Tau and Paired Helical Filament Tau. Methods in Mol Med 32, 361-373.
30. Sato, S., Cerny, R. L., Buescher, J. L., and Ikezu, T. (2006). Tau-tubulin kinase 1 (TTBK1), a neuron-specific tau kinase candidate, is involved in tau phosphorylation and aggregation. J Neurochem 9, 1573-1584.
31. Hanger, D. P., Byers, H. L., Wray, S., Leung, K-Y., Saxton, M. J., Seereeram, A., Reynolds, C. H., Ward, M. A., and Anderton, B. H. (2007). Novel phosphorylation sites in tau from Alzheimer brain support a role for casein kinase 1 in disease pathogenesis. J Biochem 282, 23645-23654.
32. Wang, J-Z., Grundke-Iqbal, I., and Iqbal, K. (2007). Kinases and phosphatases and tau sites Involved in Alzheimer neurofibrillary degeneration. Eur J Neurosci 25, 59-68.
33. Mattson, N., Zegers, I., Andreasson, U., Bjerke, M., Blankenstein, M. A., Bowser, R., Carrillo, M. C., Gobomd, J., Heath, T., Jenkins, R., Jeromin, A., Kaplow, J., Kidd, D., Laterza, O. F., Lockhart, A., Lunn, M. P., Martone, R. L., Mills, K., Pannee, J., Ratcliffe, M., Shaw, L. M., Simon, A. J., Soares, H., Teunissen, C. E., Verbeek, M. M., Umek, R. M., Vanderstichele, H., Zetterberg, H., Blennow, K., and Portelius, E. (2012). Reference measurement procedures for Alzheimer's disease cerebrospinal fluid biomarkers: definitions and approaches with focus on amyloid beta 42. Biomark Med 6, 409-417.
34. Ost, M., Nylen, K., Csajbok, L., Ohrfelt, A. O., Tullberg, M., Wikkelso, C., Nellgard, P., Rosengren, L., Blennow, K., and Nellgard, B. (2006). Initial CSF total tau correlates with 1-year outcome in patients with traumatic brain injury. Neurology 67, 1600-1604.
35. Liliang, P. C., Liang, C. L., Weng, H. C., Lu, K., Wang, K. W., Chen, H. J., and Chuang, J. H. (2010). Tau proteins in serum predict outcome after severe traumatic brain injury. J Surg Res 160, 302-307.
36. Rostami, E., Davidsson, J., Ng, K. C., Lu, J., Gyorgy, A., Walker, J., Wingo, D., Plantman, S., Bellander, B., Agoston, D. V., and Risling, M. (2012). A model for mild traumatic brain injury that induces limited transient memory impairment and increased levels of axon related serum biomarkers. Front Neurol 3, 115.
37. Corsellis, J. A., Bruton, C. J., and Freeman-Browne, D. (1973). The aftermath of boxing. Psychol Med 3, 270-303.
38. Roberts, G. W., Allsop, D., and Bruton, C. (1990). The occult aftermath of boxing. J Neurol Neurosurg Psychiatr 53, 373-378.
39. Dale, G. E., Leigh, P. N., Luthert, P., Anderton, B. H., and Roberts, G. W. (1991). Neurofibrillary tangles in dementia pugilistica are ubiquitinated. J Neurol Neurosurg Psychiatr 54, 116-118.
40. Geddes, J. F., Vowles, G. H., Nicoll, J. A., and Revesz, T. (1999). Neuronal cytoskeletal changes are an early consequence of repetitive head injury. Acta Neuropathol 98, 171-178.
41. McKee, A. C., Cantu, R. C., Nowinski, C. J., Hedley-Whyte, E. T., Gavett, B. E., Budson, A. E., Santini, V. E., Lee, H. S., Kubilus, C. A., and Stern, R. A. (2009).

Chronic traumatic encephalopathy in athletes: progressive tauopathy after repetitive head injury. J Neuropathol Exp Neurol 68, 709-735.
42. McKee, A. C., Stein, T. D., Nowinski, C. J., Stern, R. A., Daneshvar, D. H., Alvarez, V. E., Lee, H. S., Hall, G., Wojtowicz, S. M., Baugh, C. M., Riley, D. O., Kubilus, C. A., Cormier, K. A., Jacobs, M. A., Martin, B. R., Abraham, C. R., Ikezu, T., Reichard, R. R., Wolozin, B. L., Budson, A. E., Goldstein, L. E., Kowalk, N. W., and Cantu, R. C. (2013). The spectrum of disease in chronic traumatic encephalopathy. Brain 136, 43-64.
43. Jordan, B. D., Kanik, A. B., Horwich, M. S., Sweeney, D., Relkin, N. R., Petito, C. K., and Gandy, S. (1995). Apolipoprotein E epsilon 4 and fatal cerebral amyloid angiopathy associated with dementia pugilistica. Ann Neurol 38, 698-699.
44. McKenzie, K. J., McLellan, D. R., Gentleman, S. M., Maxwell, W. L., Gennarelli, T. A., and Graham, D. I. (1996). Is beta-APP a marker of axonal damage in short-surviving head injury? Acta Neuropathol 92, 608-613.
45. Nowak, L. A., Smith, G. G., and Reyes, P. F. (2009). Dementia in a retired world boxing champion: case report and literature review. Clin Neuropathol 28, 275-280.
46. Omalu, B. I., Fitzsimmons, R. P., Hammers, J., and Bailes, J. (2010). Chronic traumatic encephalopathy in a professional american wrestler. J Forensic Nursing 6, 130-136.
47. Smith, D. H., Johnson, V. E., and Stewart, W. (2013). Chronic neuropathologies of single and repetitive TBI: substrates of dementia? Nature Rev Neurol 9, 211-221.
48. Gabbita, S. P., Scheff, S. W., Menard, R. M., Roberts, K., Fugaccia, I., and Zemlan, F. P. (2005). Cleaved-tau: a biomarker of neuronal damage after traumatic brain injury. J Neurotrauma 22, 83-94.
49. Liliang, P. C., Liang, C. L., Lu, K., Wang, K. W., Weng, H. C., Hsieh, C. H., Tsai, Y-D., and Chen, H-J. (2010). Relationship between injury severity and serum tau protein levels in traumatic brain injured rats. Resuscitation 81, 1205-1208.
50. Chang, B., Gray, P., Piltch, M., Bulgin, M. S., Sorensen-Melson, S., Miller, M. W., Davies, P., Brown, D. R., Coughlin, D. R., and Rubenstein, R. (2009). Surround optical fiber immunoassay (SOFIA): more than an ultrasensitive assay for PrP detection. J Virol Methods 159, 15-22.
51. Rubenstein, R., Chang, B., Gray, P., Piltch, M., Bulgin, M. S., Sorensen-Melson, S., and Miller, M. W. (2010). A novel method for preclinical detection of PrP$^{Sc}$ in blood. J Gen Virol 91, 1883-1892.
52. Rubenstein, R., Chang, B., Gray, P., Piltch, M., Bulgin, M., Sorensen-Melson, S., and Miller, M. W. (2011). Prion disease detection, PMCA kinetics, and IgG in urine from naturally/experimentally infected scrapie sheep and pre-clinical/clinical CWD deer. J Virol 85, 9031-9038.
53. Rubenstein, R., Bulgin, M. S., Chang, B., Sorensen-Melson, S., Petersen, R. B., and LaFauci, G. (2012). PrPSc detection and infectivity in semen from scrapie-infected sheep. J Gen Virol 93, 1375-1383.
54. Rubenstein, R., and Chang, B. (2013). Re-Assessment of PrP$^{Sc}$ distribution in sporadic and variant CJD. PLoS ONE 8, e66352. doi: 10.1371/journal.pone.0066352.
55. Acker, C. M., Forest, S. K., Zinkowski, R., Davies, P., and d'Abramo, C. (2013). Sensitive quantitative assays for tau and phosphor-tau in transgenic mouse models. Neurobiol Aging 34, 338-350.
56. Schweitzer, B., Wiltshire, S., Lambert, J., O'Malley, S., Kukanskia, K., Zhu, Z., Kingsmore, S. F., Lizardi, P. M., and Ward, D. C. (2000). Immunoassays with rolling circle DNA amplification: a versatile platform for ultrasensitive antigen detection. Proc Natl Acad Sci USA 97, 10113-10119.
57. Rankin, C. A., Sun, Q., and Gamblin, T. C. (2007). Tau phosphorylation by GSK-3β promotes tangle-like filament morphology. Mol Neurodegen 2, 12.
58. Lewis, J., McGowan, E., Rockwood, J., Melrose, H., Nacharaju, P., Van Slegtenhorst, M., Gwinn-Hardy, K., Murphy, M. P., Baker, M., Yu, X., Duff, K., Hardy, J., Corral, A., Lin, W-L., Yen, S-H., Dickson, D. W., Davies, P., and Hutton, M. (2000). Neurofibrillary tangles, amyotrophy and progressive motor disturbance in mice expressing mutant (P301L) tau protein. Nat Genet 25, 402-405.
59. Dawson, H. N., Ferreira, A., Eyster, M. V., Ghoshal, N., Binder, L. I., and Vitek, M. P. (2001). Inhibition of neuronal maturation in primary hippocampal neurons from tau deficient mice. J Cell Sci 114, 1179-1187.
60. Grundke-Iqbal, I., Iqbal, K., Quinlan, M., Tung, Y. C., Zaidi, M. S., and Wisniewski, H. M. (1986). Microtubule-associated protein tau. A component of Alzheimer paired helical filaments. J Biol Chem 261, 6084-6089.
61. Nukina, N., and Ihara, Y. (1986). One of the antigenic determinants of paired helical filaments is related to tau protein. J Biochem 99, 1541-1544.
62. Wood, J. G., Mirra, S. S., Pollock, N. J., and Binder, L. I. (1986). Neurofibrillary tangles of Alzheimer disease share antigenic determinants with the axonal microtubule-associated protein tau. Proc Natl Acad Sci USA 83, 4040-4043.
63. Kondo, J., Honda, T., Mori, H., Hamada, Y., Miura, R., Ogawara, M., and Ihara, Y. (1988). The carboxyl third of tau is tightly bound to paired helical filaments. Neuron 1, 827-834.
64. Lee, V. M., Balin, B. J., Otvos, L. Jr., and Trojanowski, J. Q. (1991). A68: a major subunit of paired helical filaments and derivatized forms of normal Tau. Science 251, 675-678.
65. Lee, V. M., Goedert, M., and Trojanowski, J. Q. (2001). Neurodegenerative tauopathies Ann Rev Neurosci 24, 1121-1159.
66. Omalu, B., Bailes, J., Hamilton, R. L., Kamboh, M. I., Hammers, J., Case, M., and Fitzsimmons, R. (2011). Emerging histomorphologic phenotypes of chronic traumatic encephalopathy in American athletes. Neurosurgery 69, 173-183.
67. Rajput, A., Dickson, D. W., Robinson, C. A., Ross, O. A., Dachsel, J. C., Lincoln, S. J., Cobb, S. A., Rajput, M. L., and Farrer, M. J. (2006). Parkinsonism, Lrrk2 G2019S, and tau neuropathology. Neurology 67, 1506-1508.
68. Santpere, G., and Ferrer, I. (2009). LRRK2 and neurodegeneration. Acta Neuropathol. 117, 227-246.
69. Ihara, Y. (2001). PHF and PHF-like fibrils—cause or consequence? Neurol Aging 22, 123-126.
70. Giannakopoulos, P., Herrmann, F. R., Bussiere, T., Bouras, C., Kovari, E., Perl, D. P., Morrison, J. H., Gold, G., and Hof, P. R. (2003). Tangle and neuron numbers, but not amyloid load, predict cognitive status in Alzheimer's disease. Neurology 60, 1495-1500.
71. Shahim, P., Tegner, Y., Wilson, D. H., Randall, J., Skillback, T., Pazooki, D., Kallberg, B., Blennow, K., and Zetterberg, H. (2014). Blood biomarkers for brain injury in concussed professional ice hockey players. JAMA Neurol doi:10.1001/jamaneurol.2014.367.

72. Woertgen, C., Rothoerl, R. D., and Brawanski, A. (2001). Neuron-specific enolase serum levels after controlled cortical impact injury in the rat. J Neurotrauma 18, 569-573.
73. Woertgen, C., Rothoerl, R. D., Wiesmann, M., Missler, U., and Brawanski, A. (2002). Glial and neuronal serum markers after controlled cortical impact injury in the rat. Acta Neurochir Suppl 81, 205-207.
74. Rothermundt, M., Peters, M., Prehn, J. H., and Arolt, V. (2003). S100B in brain damage and neurodegeneration. Microsc Res Tech 60, 614-632.
75. Ross, S. A., Cunningham, R. T., Johnston, C. F., and Rowlands, B. J. (1996). NSE as an aid to outcome prediction in head injury. Br J Neurosurg 10, 471-476.
76. Pelinka, L. E., Kroepfl, A., Schmidhammer, R., Krenn, M., Buchinger, W., Redl, H., and Raabe, A. (2004). Glial fibrillary acidic protein in serum after traumatic brain injury and multiple trauma. J Trauma 57, 1006-1012.
77. Honda, M., Tsuruta, R., Kaneko, T., Kasaoka, S., Yagi, T., Todani, M., Fujita, M., Izumi, T., and Meekawa, T. (2010). Serum glial fibrillary acidic protein is a highly specific biomarker for traumatic brain injury in humans compared with 5-100B and neuron-specific enolase. J Trauma 69, 104-109.
78. Papa, L., Lewis, L. M., Falk, J. L., Zhang, Z., Silvestri, S., Giordano, P., Brophy, G. M., Demery, J. A., Dixit, N. K., Ferguson, I., Liu, M. C., Mo, J., Akinyi, L., Schmid, K., Mondello, S., Robertson, C. S., Tortella, F. C., Hayes, R. L., and Wang, K. K. W. (2012a). Elevated levels of serum glial fibrillary acidic protein breakdown products in mild and moderate traumatic brain injury are associated with intracranial lesions and neurosurgical intervention Ann Emerg Med 59, 471-483.
79. Okonkwo, D. O., Yue, J. K., Puccio, A. M., Panczykowski, D. M., Inoue, T., McMahon, P. J., Sorani, M. D., Yuh, E. L., Lingsma, H. F., Maas, A. I. R., Valadka, A. B., Manley, G. T., and Transforming Research and Clinical Knowledge in Traumatic Brain Injury investigators including, Casey, S. S., Cheong, M., Cooper, S. R., Dams-O'Connor, K., Gordon, W. A., Hricik, A. J., Hochberger, K., Menon, D. K., Mukherjee, P., Sinha, T. K., Schnyer, D. M. and Vassar, M. J. (2013). GFAP-BDP as an Acute Diagnostic Marker in Traumatic Brain Injury: Results from the Prospective Transforming Research and Clinical Knowledge in Traumatic Brain Injury Study. J Neurotrauma 30, 1490-1497.
80. Papa, L., Lewis, L. M., Silvestri, S., Falk, J. L., Giordano, P., Brophy, G. M., Demery, J. A., Liu, M. C., Mo, J., Akinyi, L., Mondello, S., Schmid, K., Robertson, C., Tortella, F. C., Hayes, R. L., and Wang, K. K. W. (2012b). Serum levels of ubiquitin C-terminal hydrolase distinguish mild traumatic brain injury from trauma controls and are elevated in mild and moderate traumatic brain injury patients with intracranial lesions and neurosurgical intervention. J Trauma Acute Care Surg 72, 1335-1344.
81. Diaz-Arrastia, R., Wang, K. K. W., Papa, L., Sorani, M. D., Yue, J. K., Puccio, A. M., McMahon, P. J., Inoue, T., Yuh, E. L., Lingsma, H. F., Maas, A. I. R., Valadka, A. B., Okonkwo, D. O., Manley, G. T., and the TRACK-TBI Investigators including Casey, S. S., Cheong, M., Cooper, S. R., Dams-O'Connor, K., Gordon, W. A., Hricik, A. J., Menon, D. K., Mukherjee, P., Schnyer, D. M., Sinha, T. K., and Vassar, M. J. (2014). Acute biomarkers of traumatic brain injury: relationship between plasma levels of ubiquitin C-terminal hydrolase-L1 (UCH-L1) and glial fibrillary acidic protein (GFAP). J Neurotrauma 31, 19-25.
82. Ma, M., Lindsell, C. J., Rosenberry, C. M., Shaw, G. J., and Zemlan, F. P. (2008). Serum cleaved tau does not predict postconcussion syndrome after mild traumatic brain injury. Am J Emerg Med 26, 763-768.
83. Fleminger, S., Oliver, D. L., Lovestone, S., Rabe-Hesketh, S., and Giora, A. (2003). Head injury as a risk factor for Alzheimer's disease: the evidence 10 years on; a partial replication. J Neurol Neurosurg Psychiatr 74, 857-862.
84. Johnson, V. E., Stewart, W., and Smith, D. H. (2012). Widespread tau and amyloid-Beta pathology many years after a single traumatic brain injury in humans. Brain Pathol 22, 142-149.
85. Smith, C., Graham, D. I., Murray, L. S., and Nicoll, J. A. (2003). Tau immunohistochemistry in acute brain injury. Neuropathol Appl Neurobiol 29, 496-502.
86. Uryu, K., Chen, X. H., Martinez, D., Browne, K. D., Johnson, V. E., Graham, D. I., Lee, V. M-Y., Trojanowski, J. Q., and Smith, D. H. (2007). Multiple proteins implicated in neurodegenerative diseases accumulate in axons after brain trauma in humans. Exp Neurol 208, 185-192.
87. Czeiter, E., Mondello, S., Kovacs, N., Sandor, J., Gabrielli, A., Schmid, K., Tortella, F., Wang, K. K. W., Hayes, R. L., Barzo, P., Ezer, E., Doczi, T., and Buki, A. (2012). Brain injury biomarkers may improve the predictive power of the IMPACT outcome calculator. J Neurotrauma 29, 1770-1778.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An ultrasensitive assay for quantifying total tau (T-tau) and/or phosphorylated tau (P-tau) in a biological sample, comprising:
   a) obtaining a biological sample from a subject;
   b) contacting said sample with capture antibodies that are immunologically specific for P-tau or T-tau, said capture antibodies binding said T-tau or P-tau when present in the sample;
   c) contacting said antibody-bound total tau or phosphorylated tau with a biotinylated detection antibody;
   d) contacting antibody-tau complexes formed in step c) with streptavidin; said streptavidin binding any biotinylated antibody in said antibody complexes;
   e) contacting the streptavidin-biotin-antibody complexes of step d) with a biotinylated primer, a T4 DNA ligase-pretreated DNA template, DNA polymerase reaction buffer, bovine serum albumin, nucleotide triphosphates supplemented with dUTP-sulforhodamine 101 acid chloride and DNA polymerase thereby forming a reaction mixture, under conditions suitable for rolling circle amplification (RCA) to occur, thereby generating a fluorescent signal;
   f) neutralizing said reaction mixture; and
   g) subjecting the mixture of step f) to fluorescence analysis using surround optical detection, thereby quantifying the levels of total tau and/or phosphorylated tau in said sample.

2. The assay of claim 1, wherein said biological sample is obtained from a subject having a traumatic brain injury (TBI).

3. The assay of claim 2, wherein said sample is obtained within one hour of said TBI.

4. The assay of claim 2, said sample is obtained at one hour, one day, one week, two weeks, three weeks, four weeks or six months after said TBI.

5. The assay of claim 2, wherein the severity of said traumatic brain injury is determined to be mild traumatic brain injury or moderate traumatic brain injury.

6. The assay of claim 1, further comprising administering a compound to said subject prior to said obtaining step.

7. The assay of claim 2, wherein said assay is performed after treatment of said TBI, for assessing efficacy of said treatment.

8. The assay of claim 1, wherein said tau-binding capture antibodies bind a site on tau selected from amino acids 150-190 on tau, a phosphorylated serine at position 202 on P-tau, or phosphorylated threonine at position 231 on P-tau.

9. The method of claim 1, wherein said method is performed on a multi-well plate, comprising separate wells coated with antibodies that bind phosphorylated tau or total tau.

10. The assay of claim 1, further comprising correlating said quantity of P-tau with CT scan normality, or a Glasgow Coma Score (GCS).

11. The assay of claim 1, further comprising measuring one or more additional biomarkers.

12. The assay of claim 1, wherein said biological sample is obtained from a subject lacking a traumatic brain injury (TBI).

* * * * *

UNITED STATES PATENT AND TRADEMARK OFFICE
CERTIFICATE OF CORRECTION

PATENT NO. : 10,295,548 B2  
APPLICATION NO. : 14/871232  
DATED : May 21, 2019  
INVENTOR(S) : Richard Rubenstein Page 1 of 1

It is certified that error appears in the above-identified patent and that said Letters Patent is hereby corrected as shown below:

In the Specification

Column 1, after Line 11 and before the heading "FIELD OF THE INVENTION", insert the following heading and paragraph:
--GOVERNMENT SUPPORT CLAUSE
This invention was made with government support under grant number W81XWH-11-2-0069 awarded by U.S. Army Medical Research Acquisition Activity. The government has certain rights in the invention.--

Signed and Sealed this
First Day of September, 2020

Andrei Iancu
*Director of the United States Patent and Trademark Office*